(12) United States Patent
Hutt et al.

(10) Patent No.: US 9,908,877 B2
(45) Date of Patent: Mar. 6, 2018

(54) IMIDAZO[1,5-A]PYRIDINIUM ION FLUOROPHORES, AND METHODS OF MAKING AND USING THE SAME

(71) Applicant: Indiana University Research and Technology Corporation, Indianapolis, IN (US)

(72) Inventors: Johnathon T. Hutt, Bloomington, IN (US); Zachary D. Aaron, Bloomington, IN (US); Dongwhan Lee, Bloomington, IN (US); Junyong Jo, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 65 days.

(21) Appl. No.: 15/157,947

(22) Filed: May 18, 2016

(65) Prior Publication Data
US 2016/0264571 A1    Sep. 15, 2016

Related U.S. Application Data

(62) Division of application No. 13/784,150, filed on Mar. 4, 2013, now Pat. No. 9,371,448.

(51) Int. Cl.
| | | |
|---|---|---|
| C12Q 1/02 | (2006.01) |
| C07D 471/04 | (2006.01) |
| C09B 57/00 | (2006.01) |
| G01N 21/64 | (2006.01) |
| G01N 33/58 | (2006.01) |

(52) U.S. Cl.
CPC .......... *C07D 471/04* (2013.01); *C09B 57/00* (2013.01); *G01N 21/6428* (2013.01); *G01N 33/582* (2013.01); *G01N 2021/6439* (2013.01)

(58) Field of Classification Search
CPC .......... C07D 471/04; G01N 21/6428; G01N 33/582; G01N 2021/6439; C09B 57/00
See application file for complete search history.

(56) References Cited

PUBLICATIONS

Hutt et al. Organic Lett. (2012) 14(12): 3162-3165; published on the Web Jun. 6, 2012.*

Johnathon Hutt, Zachary Aron "Efficient, Single-Step Access to Imidazo[1,5-a] pyridine N-Heterocyclic Carbene Precursors," Organic Letters, 13:19, Oct. 7, 2011, pp. 5256-5269 (5 pages).
Arindam Mukherjee, Shanta Dhar, Munirathinam Nethaji, Akhil R. Charkravarty "Ternary Iron (II) Complex with an Emmissive Imidazopyridine Arm from Schiff Base Cyclizations and its Oxidative DNA Cleavage Activity," Dalton Trans., 2005, Dec. 6, 2004, pp. 349-353 (5 pages).
Mithun Roy, Balabhadrapatruni V.S.K. Chakravarthi, Chelliah Jayabaskaran, Anjali A. Karande, Akil R. Chakravarty "Impact of Metal Binding on the Antitumor Activity and Cellular Imaging of a Metal Chelator Cationic Imidazopyridine Derivative," Dalton Trans., Mar. 24, 2011, 40, pp. 4855-4864 (10 pages).
Scifinder Entry Nos. 1014625-24-1 and 16722-51-3, $C_{23}H_{30}N_3 C_7 H_7O_3S$, Imidazo[5,1-a]isoquinolinium, 2-cyclohexyl-1-(cyclohexylamino)-,4-methylbenzenesulfonate (1:1) (prior to Mar. 2012).
Scifinder Entry No. 1093648-40-8 (Component: 1093729-90-8), $C_{23} H_{25} N_2 O_4$. I, Imidazo[5,1-a]isoquinolinium, 1-(3,4-dimethoxyphenyl)-8,9-dimethoxy-2,3-dimethyl-, iodide (1:1) (prior to Mar. 2012).
Scifinder Entry No. 229497-07-8, (Component: 765885-46-9), $C_{23}H_{20}C_{13}N_4$. Cl, Imidazo[1,5-a]pyridinium, 7-chloro-3-(4-chlorophenyl)-1-[[(4-chlorophenyl)(methylimino)methyl]amino]-2,8-dimethyl-, chloride (1:1) (prior to Mar. 2012).
Scifinder Entry No. 1219622-51-1, $C_{27}H_{20}BrN_3O$ S, Imidazo[1,5-a]pyridinium, 1-[[(4-bromophenyl)amino]thioxomethyl]-2-(4-methoxyphenyl)-3-phenyl-, inner salt (prior to Mar. 2012).

* cited by examiner

*Primary Examiner* — Susan M Hanley
(74) *Attorney, Agent, or Firm* — Allison Johnson, P.A.

(57) ABSTRACT

A fluorophore and methods of detecting cations and hydrophobic environments using the fluorophore are disclosed. The fluorophore includes an imidazo[1,5-a]pyridinium ion core and has the formula

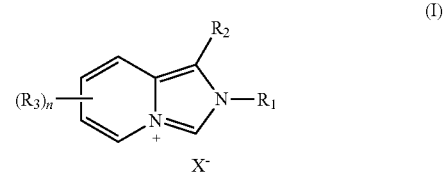

(I)

where $R_1$, $R_2$, $R_3$ and $X^-$ are as defined in the specification, and n is an integer from 1 to 4.

23 Claims, 9 Drawing Sheets

IMIDAZO[1,5-A]PYRIDINIUM ION FLUOROPHORES, AND METHODS OF MAKING AND USING THE SAME

CROSS REFERENCE TO RELATED APPLICATIONS

This application is a divisional application of U.S. patent application Ser. No. 13/784,150, filed on Mar. 4, 2013 now U.S. Pat. No. 9,371,448, and incorporated herein.

GOVERNMENT INTERESTS

This invention was made with United States government support under grant number W911NF-07-1-0533 awarded by the Department of Defense. The federal government has certain rights in the invention.

BACKGROUND

The invention relates to preparing imidazo[1,5-a]pyridinium ion fluorophores and detecting cations and hydrophobic components.

Small molecule fluorophores are becoming important tools for visualizing analytes of biological relevance. Quantitative data about the analytes is often obtained by detecting changes in the fluorescence emission of select probe molecules that bind them, which can result from photoinduced electron transfer (PET) or intramolecular charge transfer (ICT). The fluorophores that are often used for these analyses are BODIPY, coumarin, naphthalimide, and fluorescein. Although these fluorophores theoretically can be modified to display either a ratiometric dual-emission response through ICT, or a change in fluorescence intensity through PET, modifying the structure of these compounds to selectively control the excited-state photophyscial properties of these compounds typically requires multi-step synthetic operations that result in low yields.

For fluorescent probes to operate successfully and universally in a biological system, the probe must exhibit water solubility, insensitivity to local polarity, and minimal interference from background emission. These requirements are difficult to achieve.

SUMMARY

In one aspect, the invention features a fluorophore that includes a compound that includes an imidazo[1,5-a]pyridinium ion core and having the formula

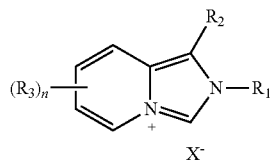

(I)

wherein $R_1$ is alkyl, aryl, arylalkyl, glycoalkyl, haloalkyl, heteroaryl, heterocyclyl, or cycloalkyl, and when $R_1$ is aryl, heteroaryl, heterocyclyl, or cycloalkyl, $R_1$ optionally is substituted with at least one $R_4$, $R_2$ is H, alkyl, aryl, arylalkyl, carbonyl, cycloalkyl, cycloalkoxy, ether, thioether, halogen, haloalkyl, heteroaryl, or heterocyclyl, and when $R_2$ is aryl, heteroaryl, heterocyclyl or cycloalkyl, $R_2$ optionally is substituted with at least one $R_4$, $R_3$ is

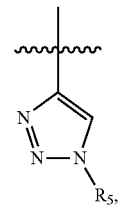

H, alkyl, alkoxy, alkenyl alkenoxy, alkynyl, alkynoxy, amide, amidino, amine, aryl, arylalkyl, azido, azo, carbamate, carbamide, carbonyl, carboxamido, carboxy, cycloalkyl, cycloalkoxy, ether, thioether, halogen, haloalkyl, heteroaryl, heterocyclyl, hydrazine, imino, nitro, phosphate, sulfate, sulfonamide, sulfonyl, sulfide, or thiocarbonyl, and when $R_3$ is alkenyl, alkenoxy, alkynyl, alkynoxy, aryl, heteroaryl, heterocyclyl or cycloalkyl, $R_3$ optionally is substituted with at least one $R_4$, each $R_4$ is independently H, alkyl, alkoxy, alkenyl, alkenoxy, alkynyl, alkynoxy, amide, amidino, amino, aryl, arylalkyl, azido, azo, carbamate, carbamide, carbonyl, carboxamido, carboxy, cycloalkyl, cycloalkoxy, cyano, ether, thioether, halogen, haloalkyl, heteroaryl, heterocyclyl, hydrazine, imino, nitro, phosphate, sulfate, sulfonamide, sulfonyl, sulfide, or thiocarbonyl, each $R_5$ is independently H, aryl, heteroaryl, ether, thioether, alkyl, alkenyl, arylalkyl, cycloalkyl, haloalkyl, heteroaryl, or heterocyclyl, and when $R_5$ is alkenyl, aryl, heteroaryl, heterocyclyl or cycloalkyl, $R_5$ optionally is substituted with at least one $R_4$, $X^-$ is a counter ion, and n is an integer from 1 to 4, the compound including at least one substituent that includes a heteroatom that includes at least one pair of electrons conjugated to the imidazo[1,5-a]pyridinium ion core, an aryl that includes a substituent that includes at least one pair of electrons conjugated to the aryl,

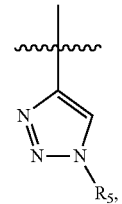

an alkenyl, an alkynyl, or a combination thereof, and when $R_1$ includes phenylalkoxy or phenylcyano, at least one of $R_2$ and $R_3$ is other than H.

In one embodiment, $R_1$ is $C_{1-4}$ alkyl, phenyl$C_{1-4}$ alkyl, phenyl$C_{1-4}$ alkoxy, or phenyl$C_{1-4}$ dialkylamine, $R_2$ is H, $C_{1-4}$ alkyl, phenyl$C_{1-4}$ alkyl, phenyl$C_{1-4}$ alkoxy, or phenyl$C_{1-4}$ dialkylamine, and $R_3$ is H, $C_{1-4}$ alkyl, phenyl$C_{1-4}$ alkyl, phenyl$C_{1-4}$ alkoxy, or dialkylamine. In another embodiment, $R_5$ is

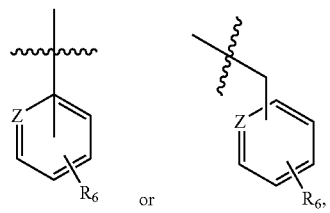

each Z is independently CH or N, and each $R_6$ is independently alkyl, alkoxy, amine, aryl, heteroaryl, halo, haloalkyl, hydrogen, nitro, carboxy, ester, ether, thioether, phosphate, sulfate, sulfonamide, sulfonyl, sulfide, or thiocarbonyl, optionally substituted with at least one $R_4$.

In other embodiments, at least one of $R_1$, $R_2$ and $R_3$ is phenyl(diacetic acid)amine, phenyl(dimethylpyridyl)amine, phenyl(methylpyridyl)(methylthiophene)amine, a phenyl substituted with a crown ether or a phenyl substituted with an aza crown ether.

In some embodiments, the compound exhibits a change in the intensity of the fluorescence emitted, a change in the wavelength of fluorescence emitted or a combination thereof in response to the presence of a cation.

In other embodiments, the compound binds at least two different cations.

In another embodiment, the compound has the formula

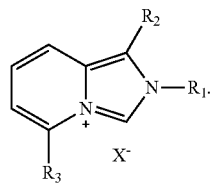

In one embodiment, $R_1$ is $C_{1-4}$ alkyl, phenyl$C_{1-4}$ alkyl, phenyl$C_{1-4}$ alkoxy, or dialkylamine, $R_2$ is H, $C_{1-4}$ alkyl, phenyl$C_{1-4}$ alkyl, phenyl$C_{1-4}$ alkoxy, or phenyl$C_{1-4}$ dialkylamine, and $R_3$ is H, $C_{1-4}$ alkyl, phenyl$C_{1-4}$ alkyl, phenyl$C_{1-4}$ alkoxy, or phenyl$C_{1-4}$ dialkylamine.

In another aspect, the invention features a cation sensor that includes a fluorophore disclosed herein. In one embodiment, the cation sensor includes a fluorophore disclosed herein in which the compound includes a first substituent that includes at least one of a heteroatom that includes at least one pair of electrons conjugated to the imidazo[1,5-a]pyridinium ion core, and an aryl that includes a second substituent that includes a heteroatom that includes at least one pair of electrons conjugated to the aryl.

In other aspects, the invention features a method of detecting a cation in a sample, the method including contacting the sample with a cation sensor, exposing the sample to radiation, and monitoring the fluorescence emission of the sample, the cation sensor including a compound that includes an imidazo[1,5-a]pyridinium ion core and having the formula

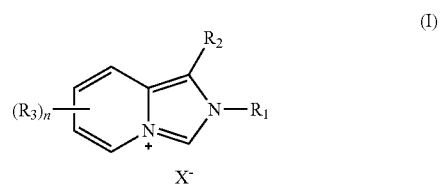

wherein $R_1$, $R_2$, $R_3$, $X^-$, n (and $R_4$ and $R_5$, where present) are as defined herein, and where at least one substituent includes a heteroatom that includes at least one pair of electrons conjugated to the imidazo[1,5-a]pyridinium ion core, an aryl that includes a second substituent that includes a heteroatom that includes at least one pair of electrons conjugated to the aryl or a combination thereof.

In one embodiment, when fluorescence emission is detected, the method further includes correlating the presence of fluorescence emission with at least one of the presence of a cation in the system, the location of a cation in the system, the concentration of a cation in the system, and the identity of a cation in the system.

In another embodiment, the method is a method of determining the pH of an aqueous system, the cation is a proton, and the method further includes correlating the emitted fluorescence to the pH of the system.

In other aspects, the invention features a compound of the formula

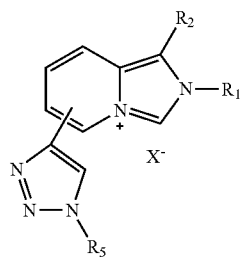

wherein $R_1$, $R_2$, $R_5$, and $X^-$ (and $R_4$, where present) are as defined herein. In some embodiments, $R_1$ is aryl. In other embodiments, $R_5$ and $R_1$ are aryl and at least one of $R_1$ and $R_5$ is arylamine. In other embodiments, $R_5$ is arylamine and $R_1$ is arylamine.

In some embodiments, the compound has the formula

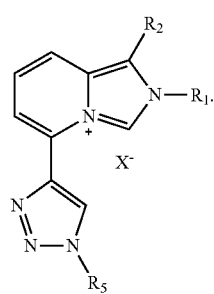

In one embodiment, $R_1$ is aryl. In some embodiments, $R_5$ and $R_1$ are aryl and at least one of $R_1$ and $R_5$ is arylamine. In another embodiment, $R_1$ is arylamine. In other embodiments, $R_5$ and $R_1$ are arylamine.

In other aspects, the invention features a method of detecting a hydrophobic component, a hydrophobic environment, or a combination thereof, the method including contacting a sample with a compound disclosed herein (e.g., a triazole-containing compound or an arylamine substituted triazole-containing compound), exposing the sample to radiation, and monitoring the fluorescence emission of the sample. In some embodiments, the method further includes correlating the emitted fluorescence to the hydrophobicity of the environment (e.g., a system).

In another aspect, the invention features a method of making a fluorophore, the method including combining alkynyl substituted 2-acylpyridine, primary amine, a formaldehyde component, and acid to form a first reaction product, and combining an azide and the first reaction product in the presence of a copper catalyst to form an triazole-substituted imidazo[1,5-a]pyridinium ion.

In other aspects, the invention features a method of determining a property of a system, the method including contacting the system with a fluorophore that includes a compound that includes an imidazo[1,5-a]pyridinium ion core and has the formula

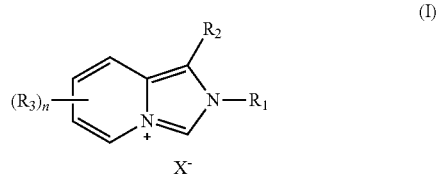

(I)

wherein $R_1$, $R_2$, $R_3$, $X^-$, and n (and $R_4$ and $R_5$, where present) are as defined herein, exposing the system to radiation, and monitoring the fluorescence emission of the system. In one embodiment, when fluorescence emission is detected, the method further includes correlating the wavelength of fluorescence emission with at least one of the presence of a cation in the system, the location of a cation in the system, the concentration of a cation in the system, the identity of a cation in the system, and the presence of a hydrophobic component in the system.

In one embodiment, the method of detecting a change in a system further includes detecting a change in at least one of the intensity of the fluorescence emission and the wavelength of fluorescence emission. In some embodiments, an increase in the intensity of the fluorescence emission indicates at least one of the presence of a cation in the system and an increase in the concentration of a cation in the system.

In another embodiment, the invention features a method of staining tissue, the method including contacting a tissue with a compound disclosed herein, exciting the compound with radiation, and detecting the fluorescence emitted by the tissue.

In one embodiment, the fluorophores, the cation sensors, the methods disclosed herein or a combination thereof includes or uses 2-(4-(diethylamino)phenyl)-2H-imidazo[1,5-a]pyridin-4-ium hexafluorophosphate, 2-butyl-1-(p-tolyl)-2H-imidazo[1,5-a]pyridin-4-ium tertraphenylborate, 2-butyl-1-(4-methoxyphenyl)-2H-imidazo[1,5-a]pyridin-4-ium chloride, 2-butyl-1-(4-(diethylamino)phenyl)-2H-imidazo[1,5-a]pyridin-4-ium tetraphenylborate, 1-(4-(diethylamino)phenyl)-2-(4-methoxyphenyl)-2H-imidazo[1,5-a]pyridin-4-ium chloride, 2-(4-(diethylamino)phenyl)-1-(4-methoxyphenyl)-2H-imidazo[1,5-a]pyridin-4-ium chloride, 2-(4-(dimethylamino)-2,6-diisopropylphenyl)-2H-imidazo[1,5-a]pyridin-4-ium tetraphenylborate, 5-(1-benzyl-1H-1,2,3-triazol-4-yl)-2-butyl-2H-imidazo[1,5-a]pyridin-4-ium tetraphenylborate, 2-butyl-5-(1-(4-(dimethylamino)phenyl)-1H-1,2,3-triazol-4-yl)-2H-imidazo[1,5-a]pyridin-4-ium tetraphenylborate, 5-(1-(4-(dimethylamino)phenyl)-1H-1,2,3-triazol-4-yl)-2-(p-tolyl)-2H-imidazo[1,5-a]pyridin-4-ium chloride, 5-(1-(4-(diethylamino)phenyl)-1H-1,2,3-triazol-4-yl)-2-(p-tolyl)-2H-imidazo[1,5-a]pyridin-4-ium chloride, 5-(1-(4-(diethylamino)phenyl)-1H-1,2,3-triazol-4-yl)-2-(4-(dimethylamino)phenyl)-2H-imidazo[1,5-a]pyridin-4-ium chloride, 5-(1-(4-(((diethylamino)methyl)phenyl)-1H-1,2,3-triazol-4-yl)-2-(4-(dimethylamino)phenyl)-2H-imidazo[1,5-a]pyridin-4-ium chloride, 2-(4-(dimethylamino)phenyl)-5-(1-(4-(trifluoromethyl)phenyl)-1H-1,2,3-triazol-4-yl)-2H-imidazo[1,5-a]pyridin-4-ium chloride, 2-(4-(dimethylamino)phenyl)-5-(1-(4-methoxyphenyl)-1H-1,2,3-triazol-4-yl)-2H-imidazo[1,5-a]pyridin-4-ium chloride, 2-(4-(diethylamino)phenyl)-5-ethynyl-2H-imidazo[1,5-a]pyridin-4-ium chloride, 2-butyl-5-ethynyl-2H-imidazo[1,5-a]pyridin-4-ium chloride, 2-(4-(dimethylamino)phenyl)-5-ethynyl-2H-imidazo[1,5-a]pyridin-4-ium chloride, 5-(4-(dimethylamino)phenyl)-2-(4-methoxyphenyl)-2H-imidazo[1,5-a]pyridin-4-ium tetraphenylborate, 2-butyl-5-(4-(dimethylamino)phenyl)-2H-imidazo[1,5-a]pyridin-4-ium tetraphenylborate, 2-(4-(diethylamino)phenyl)-3-(pyridin-2-yl)-2H-imidazo[1,5-a]pyridin-4-ium hydrogensulfate, 1-phenyl-2-(p-tolyl)-2H-imidazo[1,5-a]pyridin-4-ium hexafluorophosphate, 2-(4-(diethylamino)phenyl)-2H-imidazo[1,5-a]pyridin-4-ium hydrogensulfate, 2-(4-(diethylamino)phenyl)-5-(1-(p-tolyl)-1H-1,2,3-triazol-4-yl)-2H-imidazo[1,5-a]pyridin-4-ium chloride, and 2-(4-(dimethylamino)phenyl)-5-(1-(p-tolyl)-1H-1,2,3-triazol-4-yl)-2H-imidazo[1,5-a]pyridin-4-ium chloride, 2-butyl-5-(4-(dimethylamino)phenyl)-2H-imidazo[1,5-a]pyridin-4-ium tetraphenylborate, 5-(4-(dimethylamino)phenyl)-2-(4-methoxyphenyl)-2H-imidazo[1,5-a]pyridin-4-ium tetraphenylborate, or a combination thereof.

The invention features compounds that have a variety of uses including, e.g., as fluorophores, for detecting cations (e.g., hydrogen ions and metal ions), for detecting hydrophobic environments, for detecting hydrophobic components, and combinations thereof.

The invention also features a versatile, one pot method of synthesizing a wide variety of triazole substituted imidazo[1,5-a]pyridinium ion compounds.

Other features and advantages will be apparent from the following description of the drawings, the preferred embodiments, and from the claims.

GLOSSARY

Figure 1A:
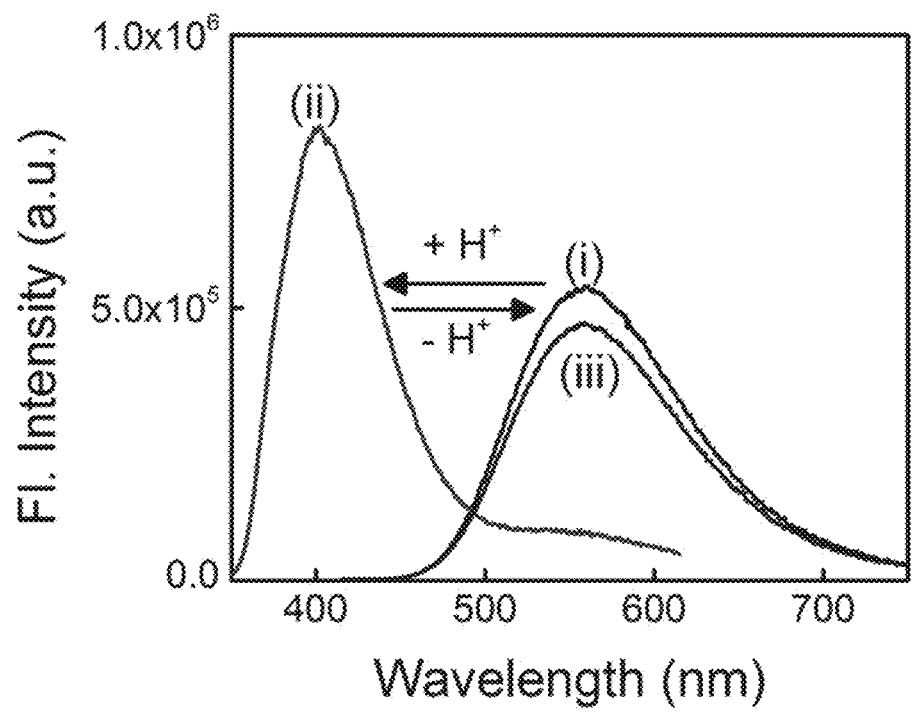
FIG. 1A is a plot of the fluorescence emission spectrum of 30 μM Compound 6 in acetonitrile prior to (i) and after (ii) the addition of 60 mM trifluoroacetic acid, and after (iii) the addition of 90 mM 1,8-diazabicyclo[5.4.0]undec-7-ene.

In reference to the invention, these terms have the meanings set forth below:

The term "C" followed by a number or a range of numbers refers to a group having the designated number of carbon atoms or having any number of carbon atoms in the designated range of numbers.

The term "alkoxy" means an alkyl group, an alkenyl group or an alkynyl group attached to an oxygen atom. Alkoxy groups include substituted and unsubstituted alkoxy groups including, e.g., methoxy, ethoxy, vinyloxy, allyloxy, and butenoxy.

The term "alkyl" means a saturated straight or branched hydrocarbon group. Alkyl groups include substituted and unsubstituted alkyl groups including, e.g., methyl, ethyl, propyl, isopropyl, 2-methyl-1-propyl, 2-methyl-2-propyl, 2-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

The term "alkenyl" means an unsaturated alkyl group having at least one double bond. Alkenyls include substituted and unsubstituted alkenyl groups including, e.g., $C_{2-6}$ alkenyls including, e.g., vinyl, allyl, 1-propenyl, isopropenyl, 2-butenyl, 2-pentenyl, 2-hexenyl, and substituted $C_{2-4}$ alkenyls.

The term "alkynyl" means an unsaturated alkyl group having at least one triple bond. Alkynyl groups include substituted and unsubstituted alkynyl groups including, e.g., ethynyl, propynyl, butynyl, pentynyl, hexynyl, methylpropynyl, 4-methyl-1-butynyl, 4-propyl-2-pentynyl, and 4-butyl-2-hexynyl.

The terms "amide" and "amido" mean a group of the form —$R^1C(O)N(R^1)$—, —$R^1C(O)N(R^1)R^1$—, or —$C(O)N(R^1)_2$, where each $R^1$ is independently selected from alkoxy, alkyl, alkenyl, alkynyl, amide, amino, aryl, arylalkyl, carbonyl, cycloalkyl, ether, haloalkyl, heteroaryl, heterocyclyl, and hydrogen. An amide can be attached to another group through the carbon, the nitrogen, or at least one R'. An amide can be cyclic, e.g., at least two $R^1$'s can be joined to form a 3- to 12-membered ring, a 3- to 10-membered ring or even a 5- to 6-membered ring. The term "carboxamido" refers to the structure —$C(O)N(R^1)_2$.

The term "amidino" means a group of the form —$C(=NR^2)N(R^2)_2$ where each $R^2$ is independently selected from alkyl, alkenyl, alkynyl, aryl, arylalkyl, cycloalkyl, haloalkyl, heteroaryl, and heterocyclyl.

The terms "amine" and "amino" mean a group of the form —$N(R^3)_2$, —$N(R^3)R^3$—, or —$R^3N(R^3)R^3$— where each $R^3$ is independently selected from alkoxy, alkyl, alkenyl, alkynyl, amide, aryl, arylalkyl, cycloalkyl, ether, haloalkyl, heteroaryl, heterocyclyl, hydrogen, and hydroxyl. An amino group can be attached to the parent molecular group through the nitrogen or at least one $R^3$. An amino group can be cyclic, for example, any two of the $R^3$'s can be joined together or with the N to form a 3- to 12-membered ring, e.g., morpholino or piperidinyl. The term amino also includes the corresponding quaternary ammonium salt of any substituted or unsubstituted amino group, e.g., —[$N(R^3)_3$]+. Amino groups include, e.g., aminoalkyl groups where at least one $R^3$ is an alkyl group.

The term "aryl" means a carbocyclic single or multiple aromatic ring system. The aromatic ring can be substituted at at least one ring position with substituents that include, e.g., alkanoyl, alkoxy, alkyl, alkenyl, alkynyl, amido, amidino, amino, aryl, arylalkyl, azido, azo, carbamate, carbamide, carbonate, carbonyl, carboxy, cyano, cycloalkyl, ester, ether, formyl, halogen, haloalkyl, heteroaryl, heterocyclyl, hydrazine, hydroxyl, imino, ketone, nitro, phosphate, phosphonato, phosphinato, sulfate, sulfide, sulfonamido, sulfonyl and thiocarbonyl. The term "aryl" also includes polycyclic ring systems having at least two cyclic rings in which at least two carbons are common to two adjoining rings (the rings are "fused rings") wherein at least one of the rings is aromatic, e.g., the other cyclic rings can be cycloalkyls, cycloalkenyls, cycloalkynyls, aryls, and combinations thereof. Aryl groups include, e.g., phenyl, tolyl, anthracenyl, fluorenyl, indenyl, azulenyl, and naphthyl, as well as benzo-fused carbocyclic moieties such as 5,6,7,8-tetrahydronaphthyl.

The term "arylalkyl" means an aryl group having at least one alkyl substituent. Arylalkyl groups include substituted and unsubstituted arylalkyl groups including, e.g., arylalkyls having a monocyclic aromatic ring system in which the ring includes 6 carbon atoms.

The term "azido" means the group —$N_3$.

The term "azo" means the group —N=N—$R^4$ where $R^4$ is selected from alkyl, alkenyl, alkynyl, aryl, arylalkyl, carbonyl, cycloalkyl, ether, haloalkyl, heteroaryl and heterocyclyl.

The term "carbamide" means the group —N($R^5$)—(CO)N($R^5$)$_2$ where each $R^5$ is independently selected from alkyl, alkenyl, alkynyl, aryl, arylalkyl, cycloalkyl, carbonyl, ether, haloalkyl, heteroaryl and heterocyclyl.

The term "carbamate" means a group of the form —$R^6$OC(O)N($R^6$)—, —$R^6$OC(O)N($R^6$)$R^6$—, or —OC(O)N($R^6$)$_2$, where each $R^6$ is independently selected from alkoxy, aryloxy, alkyl, alkenyl, alkynyl, aryl, arylalkyl, cycloalkyl, ether, formyl, haloalkyl, heteroaryl, and heterocyclyl. Carbamates include, e.g., arylcarbamates and heteroaryl carbamates, e.g., where at least one $R^5$ is independently selected from aryl (e.g., phenyl) and heteroaryl (e.g., pyridinyl).

The term "carbonyl" means the group —C(O)—$R^7$, where $R^7$ is selected from alkoxy, alkyl, alkenyl, alkynyl, amide, amidino, aryl, arylalkyl, carbamate, carbonyl, carboxy, cyano, cycloalkoxy, cycloalkyl, ether, glycoalkyl, halo, haloalkyl, heteroaryl, heterocyclyl, heterocycloalkyl, heterocyclylalkoxy, heterocyclyloxyalkyl, hydrogen, hydroxyl, hydroxyalkyl, hydrazine, azo, carbamide, imino, sulfide, and thiocarboxy.

The term "carboxy" means the group —COOH and its corresponding salts, e.g. —COONa.

The term "cyano" means the group —CN.

The term "cycloalkoxy" means a cycloalkyl group attached to an oxygen atom.

The term "cycloalkyl" means a monovalent saturated or partially unsaturated cyclic, bicyclic, or bridged bicyclic hydrocarbon group. Cycloalkyl groups include substituted and unsubstituted cycloalkyl groups including, e.g., cyclopropyl, cyclobutyl, cycloentyl, cyclohexyl, cycloheptyl, cyclooctyl, cyclo nonyl, cyclodecyl, cyclododecyl, cyclohexanes, cyclohexenes, cyclopentanes, cyclopentenes, cyclobutanes and cyclopropanes. Cycloalkyl groups can be substituted with alkanoyl, alkoxy, alkyl, alkenyl, alkynyl, amido, amidino, amino, aryl, arylalkyl, azido, azo, carbamate, carbamide, carbonate, carbonyl, carboxy, cyano, cycloalkyl, ester, ether, formyl, halogen, haloalkyl, heteroaryl, heterocyclyl, hydrazine, hydroxyl, imino, ketone, nitro, phosphate, phosphonato, phosphinato, sulfate, sulfide, sulfonamido, sulfonyl and thiocarbonyl. Cycloalkyl groups can be fused to other cycloalkyl, aryl, or heterocyclyl groups.

The term "ether" means a group having the structure —$R^8$O—$R^8$—, where each $R^8$ is independently selected from alkyl, aryl, cycloalkyl, heterocyclyl, and ether. The ether can be attached to the parent molecular group through at least one $R^7$. Ethers include substituted and unsubstituted ethers including, e.g., alkoxyalkyl groups, alkoxyaryl groups, crown ethers, and aza crown ethers (e.g., monoaza crown ethers, diaza crown ethers and triaza crown ethers). Ethers also include polyethers, e.g., where at least one $R^8$ is an ether.

The term "glycoalkyl" means acyclic and cyclic mono- and polysaccharides. The glycoalkyl is attached to the parent molecular group through an available oxygen atom forming an ether linkage.

The terms "halo" and "halogen" mean fluorine, chlorine, bromine or iodine.

The term "haloalkyl" means an alkyl group substituted with at least one halogen atom.

The term "heteroaryl" means a mono- or multi-cyclic aromatic ring system containing at least one heteroatom. Heteroaryls can also be fused to non-aromatic rings. Heteroaryl groups include substituted and unsubstituted heteroaryl groups including, e.g., acridinyl, benzimidazolyl, benzofuryl, benzothiazolyl, benzothienyl, benzoxazolyl, carbazolyl, carbolinyl, cinnolinyl, furazanyl, furyl, imidazolyl, indazolyl, indolizinyl, indolyl, isobenzofuryl, isoindolyl, isoquinolinyl, isothiazolyl, isoxazolyl, naphthyridinyl, oxadiazolyl, oxazolyl, phenanthridinyl, phenanthrolinyl, phenarsazinyl, phenazinyl, phenothiazinyl, phenoxazinyl, phthalazinyl, pteridinyl, purinyl, pyrazinyl, pyrazolyl, pyrazyl, pyridazinyl, pyridinyl, pyrimidilyl, pyrimidyl, pyrrolyl, quinolinyl, quinolizinyl, quinoxalinyl, quinoxaloyl, quinazolinyl, tetrazolyl, thiadiazolyl, thianthrenyl, thiazolyl, thienyl, thiophenyl, triazinyl, (1,2,3)- and (1,2,4)-triazolyl. The heteroaryl ring can be substituted at at least one position with such substituents as described above including, e.g., alkanoyl, alkoxy, alkyl, alkenyl, alkynyl, amido, amidino, amino, aryl, arylalkyl, azido, azo, carbamate, carbamide, carbonate, carbonyl, carboxy, cyano, cycloalkyl, ester, ether, formyl, halogen, haloalkyl, heteroaryl, heterocyclyl, hydrazine, hydroxyl, imino, ketone, nitro, phosphate, phosphonato, phosphinato, sulfate, sulfide, sulfonamido, sulfonyl and thiocarbonyl.

The term "heteroatom" means an atom that is other than carbon or hydrogen. Examples of heteroatoms include N, O, S, and P.

The terms "heterocyclyl" and "heterocyclic group" mean saturated and partially unsaturated ring structures that include from one to four heteroatoms. Heterocyclyls include substituted and unsubstituted heterocyclyl groups including, e.g., from 3- to 7-membered ring structures or even from 3- to 10-membered ring structures. Heterocycles can also be mono- or multi-cyclic ring systems. A heterocycle can be fused to at least one aryl, partially unsaturated ring or saturated ring. Heterocyclyl groups include, e.g., biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isoxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, and sultones. The heterocyclic ring can be substituted at at least one position with substituents including, e.g., alkanoyl, alkoxy, alkyl, alkenyl, alkynyl, amido, amidino, amino, aryl, arylalkyl, azido, azo, carbamate, carbamide, carbonate, carbonyl, carboxy, cyano, cycloalkyl, ester, ether, formyl, halogen, haloalkyl, heteroaryl, heterocyclyl, hydrazine, hydroxyl, imino, ketone, nitro, phosphate, phosphonato, phosphinato, sulfate, sulfide, sulfonamido, sulfonyl and thiocarbonyl.

The term "heterocycloalkyl" means a saturated heterocyclyl group attached to an alkyl group.

The term "heterocyclylalkoxy" means a heterocyclyl attached to an alkoxy group.

The term "heterocyclyloxyalkyl" means a heterocyclyl attached to an oxygen (—O—), which is attached to an alkyl group.

The term "hydrazine" means the group —N($R^9$)N($R^9$)$_2$ where each $R^9$ is independently selected from alkyl, alkenyl, alkynyl, aryl, arylalkyl, carbonyl, cycloalkyl, ether, haloalkyl, heteroaryl and heterocyclyl.

The terms "hydroxy" and "hydroxyl" means the group —OH.

The term "hydroxyalkyl" means a hydroxy group attached to an alkyl group.

The term "imino" means the group —C(=N)—$R^{10}$, where $R^{10}$ is selected from alkyl, alkenyl, alkynyl, aryl, arylalkyl, cycloalkyl, ether, haloalkyl, heteroaryl, and heterocyclyl.

The term "nitro" means the group —$NO_2$.

The term "phosphate" means the group —OP(O)($OR^{11}$)$_2$ or its anions, where each $R^{11}$ is independently selected from alkyl, alkenyl, alkynyl, aryl, arylalkyl, cycloalkyl, hydrogen, haloalkyl, heteroaryl, and heterocyclyl. The term "phosphanato" means the substituent —P(O)($OR^{11}$)$_2$ or its anions. The term "phosphinato" means the substituent $PR^{11}$(O)($OR^{11}$) or its anion.

The term "sulfate" means the group —OS(O)($OR^{12}$)$_2$ or its anions, where each $R^{12}$ is independently selected from alkyl, alkenyl, alkynyl, aryl, arylalkyl, cycloalkyl, hydrogen, haloalkyl, heteroaryl, and heterocyclyl.

The terms "sulfonamide" and "sulfonamido" mean a group having the structure —N($R^{13}$)—S(O)$_2$—$R^{13}$— or —S(O)$_2$—N($R^{13}$)$R^{13}$, where each $R^{13}$ is independently selected from hydrogen, alkyl, aryl, cycloalkyl, and heterocyclyl. Sulfonamides include substituted and unsubstituted sulfonamides including, e.g., alkylsulfonamides, arylsulfonamides, cycloalkyl sulfonamides, and heterocyclyl sulfonamides.

The term "sulfonyl" means a group having the structure $R^{14}SO_2$—, where $R^{14}$ is selected from alkyl, aryl, cycloalkyl, and heterocyclyl. The term "alkylsulfonyl" means an alkyl group attached to a sulfonyl group.

The terms "sulfide" and "thioether" means a group having the structure $R^{15}S$—, where $R^{15}$ is selected from alkyl, alkenyl, alkynyl, aryl, arylalkyl, cycloalkyl, ether, haloalkyl, heteroaryl, and heterocyclyl. The term "alkylsulfide" means an alkyl group attached to a sulfur atom. Sulfides include, e.g., "thio," which means an —SH substituent.

The terms "thiocarbonyl" and "thiocarboxy" mean a carbon connected to a sulfur atom through a double bond.

All chemical groups disclosed herein can be substituted where valence permits substitution unless otherwise specified.

"Substituted" as used herein to describe a compound or chemical moiety refers to at least one hydrogen atom of that compound or chemical moiety being replaced with a second chemical moiety. Non-limiting examples of substituents include those substituents found in the exemplary compounds and embodiments disclosed herein, and halogen, alkyl, heteroalkyl, alkenyl, alkynyl, aryl, heteroaryl, hydroxy, alkoxyl, amino, azo, hydrazine, carbamide, nitro, thiol, thioether, imine, cyano, amido, phosphonato, phosphine, carbonyl, carboxyl, thiocarbonyl, sulfonyl, sulfonamide, ketone, aldehyde, ester, haloalkyl (e.g., trifluoromethyl), cycloalkyl, heterocycloalkyl, and combinations thereof. These substituents can optionally be further substituted with a substituent selected from such groups. Substituents include, e.g., moieties in which a carbon atom is substituted with a heteroatom such as nitrogen, oxygen, silicon, phosphorus, boron, sulfur, or a halogen atom.

The naming of the R substituents with respect to the heterocyclic core is such that the group listed first is attached to the heterocyclic core.

DETAILED DESCRIPTION

The compounds disclosed herein are fluorophores (i.e., when excited by radiation of a first wavelength, they exhibit fluorescence emission at a second wavelength). The compounds include an imidazo[1,5-a]pyridinium ion core and at least one substituent attached to the core. The compounds can exhibit a change in their fluorescence emission properties due to a change in the deexcitation pathway (i.e., the mechanism by which the fluorescence emission is modulated). The change in the deexcitation pathway of the compounds can be modulated by photoinduced electron transfer (PET) or intramolecular charge transfer (ICT). A change in the deexcitation pathway can manifest itself as an increase in the intensity of the fluorescence emission, a decrease in the intensity of the fluorescence emission, a decrease in the intensity of the fluorescence emission at a first wavelength and an increase in the intensity of the fluorescence emission at a second wavelength, and combinations thereof. In some embodiments, for example, the compound responds to a change in the environment surrounding the compound (e.g., the presence, absence or change in concentration of a cation or of the hydrophobicity of the environment) by exhibiting a change in fluorescence emission due to photoinduced electron transfer when the environment is in one state and a change in fluorescence emission due to intramolecular charge transfer when the environment is in another state. This effect can be reversed upon alteration of the environment to one that mimics its initial state.

The presence and mechanism of fluorescence emission can depend upon the substituents on the compound, the nature of a binding event with an analyte, the environment in which the compound is located, and combinations thereof. The substituents on the compound can be selected to achieve compounds having a variety of fluorescence properties when excited by radiation including, e.g., compounds that inherently exhibit fluorescence emission upon excitation, compounds that do not inherently exhibit fluorescence emission but exhibit fluorescence emission upon a binding event (e.g., when the bound to a cation), compounds that exhibit fluorescence emission when present in a certain environment (e.g., a hydrophobic environment or an aqueous environment), compounds that exhibit a change in fluorescence emission in response to a change in the environment in which the compound is located, and combinations thereof. A change in a fluorescence property exhibited by a compound can manifest itself as a change in emission intensity, a change in the emission wavelength, and combinations thereof.

The substituents also can be selected to achieve compounds that function in a variety of modes including, e.g., in a "turn-on" mode in which detectable fluorescence emission occurs as the environment changes or a binding event occurs, in a "turn-off" mode in which a detectable fluorescence emission ceases to occur as the environment changes or a binding event occurs, in a ratiometric response mode in which there are detectable changes in the relative intensity of fluorescence emissions at at least two different wavelengths, and combinations thereof. These compounds can be useful as "turn-on" sensors, "turn-off" sensors, and ratiometric response sensors, respectively. At least one property of the detected fluorescence emission (e.g., the presence, absence, and intensity of the emission) can be correlated to a property of the system (e.g., the presence, absence, or concentration of a component of interest in the system).

The compounds preferably absorb radiation having a wavelength from about 250 nm to about 600 nm and emit radiation having a wavelength from about 350 nm to about 900 nm.

The compounds preferably exhibit high fluorescence quantum yield in the environment of interest including, e.g., aqueous environment, organic solvent environment, hydrophobic environment, and combinations thereof. The compounds preferably exhibit a fluorescence quantum yield of at least 0.1%, at least 1%, at least 5%, at least 10%, at least 15%, at least 20%, at least 25%, at least 30%, or even at least 50%.

The compounds can be water soluble or water insoluble and the counter ion can be selected to render the compound water soluble or water insoluble (e.g., soluble in organic solvent). The compound preferably is stable over a wide temperature range, upon exposure to oxygen, water, in mild acid, and in mild base.

Imidazo[1,5-a]Pyridinium Ions

The general chemical structure for the imidazo[1,5-a] pyridinium ions is as shown in the following formula:

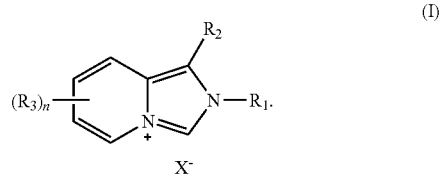

(I)

$R_1$ is alkyl, aryl, arylalkyl, glycoalkyl, haloalkyl, heteroaryl, heterocyclyl, or cycloalkyl. When $R_1$ is aryl, heteroaryl, heterocyclyl, or cycloalkyl, $R_1$ optionally can be substituted with at least one $R_4$. Specific $R_1$ groups include $C_{1-4}$ alkyl, phenyl, phenyl$C_{1-4}$ alkyl, phenyl$C_{1-4}$alkoxy, phenylamine, phenyldi-$C_{1-4}$ alkylamine, phenylhalo$C_{1-4}$alkyl, pyridyl, phenyl(dicarboxy)amine, phenyl(dimethylpyridyl) amine, phenyl(methylpyridyl)(methylthiophene)amine and phenyl(aza-crown ether).

$R_2$ is H, alkyl, aryl, arylalkyl, carbonyl, cycloalkyl, ether, thioether, halogen, haloalkyl, heteroaryl, or heterocyclyl. When $R_2$ is aryl, heteroaryl, heterocyclyl or cycloalkyl, $R_2$ optionally can be substituted with at least one $R_4$. Specific $R_2$ groups include $C_{1-4}$ alkyl, phenyl, phenyl$C_{1-4}$ alkyl, phenyl$C_{1-4}$ alkoxy, phenylamine, phenyldi-$C_{1-4}$ alkylamine, phenylhalo$C_{1-4}$alkyl, pyridyl, phenyl(dicarboxy)amine, phenyl(dimethylpyridyl)amine, phenyl(methylpyridyl)(methylthiophene)amine and phenyl(aza-crown ether).

$R_3$ is

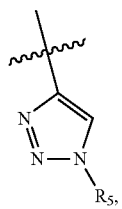

H, alkyl, alkoxy, alkenyl alkenoxy, alkynyl, alkynoxy, amide, amidino, amine, aryl, arylalkyl, azido, azo, carbamate, carbamide, carbonyl, carboxamido, carboxy, cycloalkyl, cycloalkoxy, ether, thioether, halogen, haloalkyl, heteroaryl, heterocyclyl, hydrazine, imino, nitro, phosphate, sulfate, sulfonamide, sulfonyl, sulfide, or thiocarbonyl. When $R_3$ is alkenyl, alkenoxy, alkynyl, alkynoxy, aryl, heteroaryl, heterocyclyl or cycloalkyl, $R_3$ optionally can be substituted with at least one $R_4$. Specific $R_3$ groups include $C_{1-4}$ alkyl, $C_{1-4}$ alkoxy, $C_{1-4}$ alkenyl, $C_{1-4}$ alkynyl, (di-$C_{1-4}$alkyl)amine, halogen, trihaloalkyl, phenyl, phenyl$C_{1-4}$ alkyl, phenyl$C_{1-4}$ alkoxy, phenylamine, phenyl(di-$C_{1-4}$ alkyl)amine, phenylhalo$C_{1-4}$alkyl, pyridyl, triazolyl, triazolylaryl, triazolylarylalkyl, triazolylarylalkoxy, triazolylarylamine, triazolylaryldialkylamine, phenyl(dicarboxy)amine, phenyl (dimethylpyridyl)amine, phenyl(methylpyridyl) (methylthiophene)amine and phenyl(aza-crown ether). Particularly useful $R_3$ groups include triazoles that include dialkylaniline as the $R_4$ substituent, alkynes, and azides.

Each $R_4$ is independently H, alkyl, alkoxy, alkenyl alkenoxy, alkynyl, alkynoxy, amide, amidino, amino, aryl, arylalkyl, azido, azo, carbamate, carbamide, carbonyl, carboxamido, carboxy, cyano, cycloalkyl, cycloalkoxy, ether, thioether, halogen, haloalkyl, heteroaryl, heterocyclyl, hydrazine imino, nitro, phosphate, sulfate, sulfonamide, sulfonyl, sulfide, or thiocarbonyl. Specific $R_4$ groups include hydrogen, $C_{1-4}$ alkyl, $C_{1-4}$ alkoxy, $C_{1-4}$ alkenyl, $C_{1-4}$ alkynyl, amines, $C_{1-4}$dialkylamine, amidos, halogen, trihaloalkyl, phenyl, (dicarboxy)amine, (dimethylpyridyl)amine, (methylpyridyl)(methylthiophene)amine, crown ether, and aza crown ether.

Each $R_5$ is independently H, aryl, heteroaryl, ether, thioether, alkyl, alkenyl, arylalkyl, arylamine, cycloalkyl, cycloalkoxy, haloalkyl, heteroaryl, or heterocyclyl. When $R_5$ is alkenyl, aryl, heteroaryl, heterocyclyl or cycloalkyl, $R_5$ optionally can be substituted with at least one $R_4$.

Specific examples of $R_5$ include

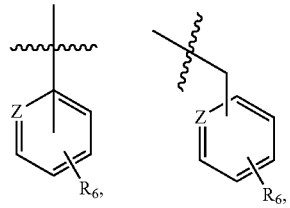

hydrogen, phenyl, phenyl$C_{1-4}$ alkyl, phenyl$C_{1-4}$ alkoxy, phenylamine, phenyldi-$C_{1-4}$ alkylamine, phenyl$C_{1-4}$alkoxy, and phenylhalo$C_{1-4}$alkyl.

Each Z is independently CH or N.

Each $R_6$ is independently alkyl, alkoxy, amine, aryl, azo, carbamide, heteroaryl, halogen, haloalkyl, hydrazine, hydrogen, nitro, carbonyl, carboxy, ester, ether, thioether, phosphate, sulfate, sulfonamide, sulfonyl, sulfide, or thiocarbonyl.

$X^-$ is a counter ion. Suitable counter ions include, e.g., any stable anionic species, chloride, fluoride, bromide, hexafluorophosphate, tetrafluoroborate, tetraphenylborate, sulfonic acid salts (e.g., sulfate bisulfate, sulfite, bisulfite, triflate, and tosylate), hydroxide, alkoxide, carboxylate (e.g., trifluoroacetate, acetate, benzoate, and hexanoate), carbonate, bicarbonate, $[B[3,5-(CF_3)_2C_6H_3]_4]^-$, perchlorate, tetrakis(pentafluorphenyl)borate, and $Al(OC(CF_3)_3)_4^-$.

The letter n on $R_3$ is an integer from 1 to 4.

The imidazo[1,5-a]pyridinium ion preferably includes at least one substituent that includes, e.g., at least one heteroatom that includes at least one electron pair conjugated to the imidazo[1,5-a]pyridinium ion core, an aryl group that includes a substituent that includes a heteroatom that includes at least one pair of electrons conjugated to the aryl group, a triazole, an alkenyl, an alkynyl, and combinations thereof. Useful electron pair donating heteroatoms include, e.g., nitrogen, oxygen, sulfur, and phosphorous.

Triazole Substituted Imidazo[1,5-a]Pyridinium Ions

One useful class of the imidazo[1,5-a]pyridinium ions of formula (I) includes imidazo[1,5-a]pyridinium ions having the general chemical structure (formula II):

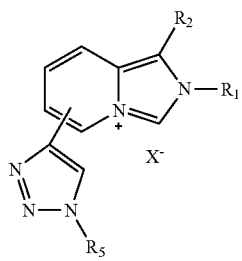

(II)

where $R_1$, $R_2$, $R_5$ and $X^-$ are as set forth above with respect to the compound of formula I. Specific examples of $R_5$ include hydrogen,

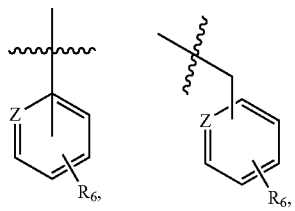

phenyl, phenyl$C_{1-4}$ alkyl, phenyl$C_{1-4}$ alkoxy, phenylamine, phenyl(di-$C_{1-4}$ alkyl)amine, phenyl$C_{1-4}$alkoxy, and phenyl-halo$C_{1-4}$alkyl, where R6 and Z are as defined above with respect to the compound of formula (I).

Specific imidazo[1,5-a]pyridinium ions include, e.g., 2-(4-(diethylamino)phenyl)-2H-imidazo[1,5-a]pyridin-4-ium hexafluorophosphate, 2-butyl-1-(p-tolyl)-2H-imidazo [1,5-a]pyridin-4-ium tertraphenylborate, 2-butyl-1-(4-methoxyphenyl)-2H-imidazo[1,5-a]pyridin-4-ium chloride, 2-butyl-1-(4-(diethylamino)phenyl)-2H-imidazo[1,5-a]pyridin-4-ium tetraphenylborate, 1-(4-(diethylamino)phenyl)-2-(4-methoxyphenyl)-2H-imidazo[1,5-a]pyridin-4-ium chloride, 2-(4-(diethylamino)phenyl)-1-(4-methoxyphenyl)-2H-imidazo[1,5-a]pyridin-4-ium chloride, 2-(4-(dimethylamino)-2,6-diisopropylphenyl)-2H-imidazo[1,5-a]pyridin-4-ium tetraphenylborate, 5-(1-benzyl-1H-1,2,3-triazol-4-yl)-2-butyl-2H-imidazo[1,5-a]pyridin-4-ium tetraphenylborate, 2-butyl-5-(1-(4-(dimethylamino)phenyl)-1H-1,2,3-triazol-4-yl)-2H-imidazo[1,5-a]pyridin-4-ium tetraphenylborate, 5-(1-(4-(dimethylamino)phenyl)-1H-1,2,3-triazol-4-yl)-2-(p-tolyl)-2H-imidazo[1,5-a]pyridin-4-ium chloride, 5-(1-(4-(diethylamino)phenyl)-1H-1,2,3-triazol-4-yl)-2-(p-tolyl)-2H-imidazo[1,5-a]pyridin-4-ium chloride, 5-(1-(4-(diethylamino)phenyl)-1H-1,2,3-triazol-4-yl)-2-(4-(dimethylamino)phenyl)-2H-imidazo[1,5-a]pyridin-4-ium chloride, 5-(1-(4-((diethylamino)methyl)phenyl)-1H-1,2,3-triazol-4-yl)-2-(4-(dimethylamino)phenyl)-2H-imidazo[1,5-a]pyridin-4-ium chloride, 2-(4-(dimethylamino)phenyl)-5-(1-(4-(trifluoromethyl)phenyl)-1H-1,2,3-triazol-4-yl)-2H-imidazo[1,5-a]pyridin-4-ium chloride, 2-(4-(dimethylamino)phenyl)-5-(1-(4-methoxyphenyl)-1H-1,2,3-triazol-4-yl)-2H-imidazo[1,5-a]pyridin-4-ium chloride, 2-(4-(diethylamino)phenyl)-5-ethynyl-2H-imidazo[1,5-a]pyridin-4-ium chloride, 2-butyl-5-ethynyl-2H-imidazo[1,5-a]pyridin-4-ium chloride, 2-(4-(dimethylamino)phenyl)-5-ethynyl-2H-imidazo[1,5-a]pyridin-4-ium chloride, 5-(4-(dimethylamino)phenyl)-2-(4-methoxyphenyl)-2H-imidazo[1,5-a]pyridin-4-ium tetraphenylborate, 2-butyl-5-(4-(dimethylamino)phenyl)-2H-imidazo[1,5-a]pyridin-4-ium tetraphenylborate, 2-(4-(diethylamino)phenyl)-3-(pyridin-2-yl)-2H-imidazo[1,5-a]pyridin-4-ium hydrogensulfate, 1-phenyl-2-(p-tolyl)-2H-imidazo[1,5-a]pyridin-4-ium hexafluorophosphate, 2-(4-(diethylamino)phenyl)-2H-imidazo[1,5-a]pyridin-4-ium hydrogensulfate, 2-(4-(diethylamino)phenyl)-5-(1-(p-tolyl)-1H-1,2,3-triazol-4-yl)-2H-imidazo[1,5-a]pyridin-4-ium chloride, 2-(4-(dimethylamino)phenyl)-5-(1-(p-tolyl)-1H-1,2,3-triazol-4-yl)-2H-imidazo[1,5-a]pyridin-4-ium chloride, 2-butyl-5-(4-(dimethylamino)phenyl)-2H-imidazo[1,5-a]pyridin-4-ium tetraphenylborate, and 5-(4-(dimethylamino)phenyl)-2-(4-methoxyphenyl)-2H-imidazo[1,5-a]pyridin-4-ium tetraphenylborate.

Methods of Use

The imidazo[1,5-a]pyridinium ions are useful in a variety of applications including, e.g., monitoring (e.g., detecting) the fluorescence emission of a system (e.g., monitoring the fluorescence emission intensity increase, decrease, and combinations thereof), detecting the presence, absence, concentration or combination thereof of a moiety including, e.g., a cation (e.g., as a cation sensor), a hydrophobic component (e.g., as a hydrophobicity sensor), and combinations thereof.

The imidazo[1,5-a]pyridinium ions can be used to monitor cations and hydrophobic components in a variety of in vitro and in vivo environments including, e.g., extracellular spaces, vesicles, vascular tissue of plants and animals, biological fluids (e.g., blood and urine), biomolecules, biological structures (e.g., cell membranes, lipid bilayers, and protein binding pockets), synthetic (i.e., artificial) membranes, micelles, dendrimers, and lipid bilayers, buffer solutions, fermentation media, environmental samples (e.g., water, soil, waste water and seawater), and in chemical reactors.

The imidazo[1,5-a]pyridinium ions can interact with the cations and hydrophobic components through a variety of mechanisms including, e.g., forming a covalent bond, forming an ionic bond, through hydrophobic interactions, through van der Waals interactions, and combinations thereof.

Cation Sensor

The substituents on the imidazo[1,5-a]pyridinium ion core of the compound of formula (I) can be selected to achieve a cation sensor useful in a variety of applications including, e.g., detecting at least one of the presence, absence, and concentration of at least one cation. The cation sensor preferably includes at least one substituent that includes, e.g., at least one heteroatom that includes at least one electron pair conjugated to the imidazo[1,5-a]pyridinium ion core, an aryl group that includes a substituent that includes a heteroatom having at least one lone pair of electrons conjugated to the aryl group, and combinations thereof.

The cation sensor can function in a variety of modes including, e.g., as a turn-on sensor, a turn-off sensor, a ratiometric response sensor, and combinations thereof. The cation sensor can exhibit a variety of fluorescence responses to a cation of interest including, e.g., being free from fluorescence emission (e.g., exhibits fluorescence quenching) in the absence of a cation of interest, exhibiting fluorescence emission in the absence of a cation of interest, exhibiting fluorescence emission in the presence of a cation of interest (i.e., turn-on), exhibiting fluorescence quenching in the presence of a cation of interest, exhibiting a ratiometric response to cation concentration, and combinations thereof. For some cation sensors that employ the compound of formula (I), the turn-on fluorescence emission is modulated by PET and the ratiometric response is modulated by ICT.

The cation sensor can be constructed to bind a variety of cations including, e.g., protons and metal ions including, e.g., $Ca^{2+}$, $Zn^{2+}$, $Mg^{2+}$, $Ga^{3+}$, $Tb^{3+}$, $La^{3+}$, $Pb^{3+}$, $Hg^{2+}$, $Cd^{2+}$, $Cu^{2+}$, $Ni^{2+}$, $Co^{2+}$, $Fe^{2+}$, $Mn^{2+}$, $Ba^{2+}$, $U^{2+}$, $U^{3+}$, and $Sr^{2+}$, and combinations thereof.

Figure 1B:
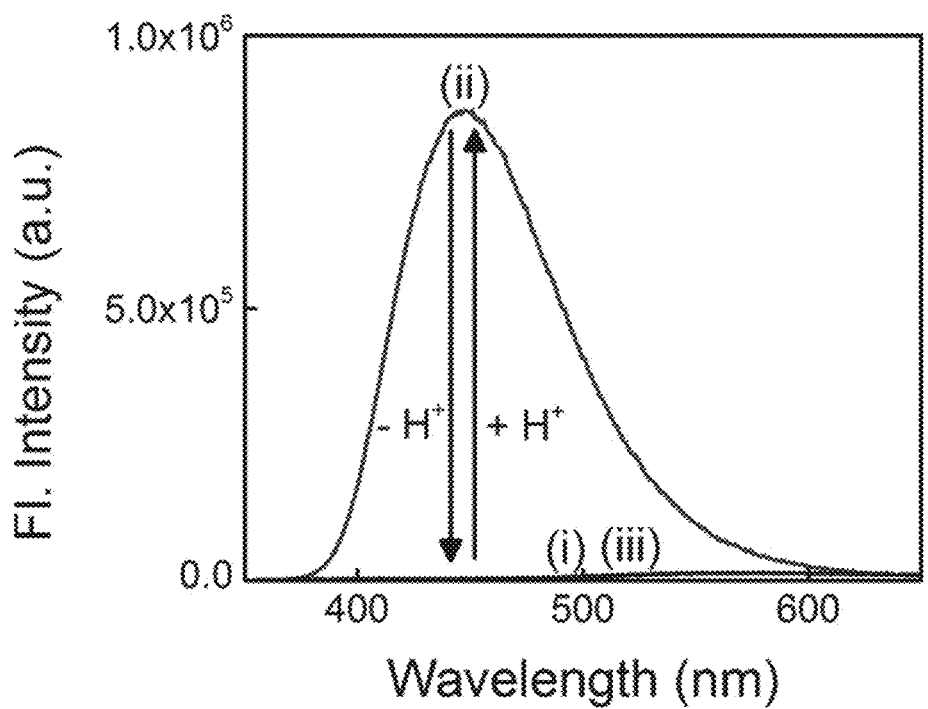
FIG. 1B is a plot of the fluorescence emission spectrum of 30 μM Compound 7 in acetonitrile prior to (i) and after (ii) the addition of 60 mM trifluoroacetic acid, and after (iii) the addition of 90 mM 1,8-diazabicyclo[5.4.0]undec-7-ene.

In one embodiment, the compound of formula (I) includes a proton binding amino group conjugated to the imidazo[1,5-a]pyridinium ion core. Such a compound can function as a pH sensor. Useful pH sensors include, e.g., compounds of formula (I) in which $R_1$ is phenyldialkylamine (e.g., 4-phenyldiethylamine), $R_2$ is phenylalkoxy, and $R_3$ is H, and compounds of formula (I) in which $R_1$ is phenylalkoxy (e.g., 4-phenylmethoxy), $R_2$ is phenyldialkylamine (e.g., 4-phenyldiethylamine), and $R_3$ is H. One example of a useful pH sensor is Compound 7 of Example 7, where $R_1$ is 4-diethylanaline and $R_2$ is 4-phenylmethoxy, which exhibits fluorescence emission at 450 nm in acetonitrile in the presence of trifluoroacetic acid, and the absence of emission (i.e., fluorescence quenching) in acetonitrile in the absence of trifluoroacetic acid (see, FIG. 1B).

The cation sensors can also exhibit a ratiometric response to changing pH. Useful pH sensors that exhibit a ratiometric response to pH in acetonitrile include, e.g., compounds of formula (I) in which $R_1$ is phenylalkoxy (e.g., 4-phenylmethoxy), $R_2$ is phenyldialkylamine (e.g., 4-phenyldiethylamine), and $R_3$ is H. One example of a useful ratiometric response sensor is Compound 6 of Example 6, where $R_2$ is 4-diethylanaline and $R_1$ 4-phenylmethoxy, which exhibits fluorescence emission at 565 nm in acetonitrile in the absence of trifluoroacetic acid, and fluorescence emission at 400 nm in acetonitrile in the presence of trifluoroacetic acid (see, FIG. 1A). The ratio of the intensity at each wavelength can be used to quantify the amount of acid present in the system.

The compound optionally includes at least two substituents capable of donating a pair of electrons to a cation (i.e., cation chelating substituents). The cation chelating substituents are capable of binding a cation such that the compound forms at least two coordinate bonds with the cation. The compound optionally includes include at least two different cation chelating moieties that have affinities for different cations and can function as a dual or multi-cation sensor. Useful dual cation chelating moieties have affinities for two cations including, e.g., $Ca^{2+}$ and $Zn^{2+}$, $Ca^{2+}$ and $Mg^{2+}$, and $Mg^{2+}$ and $Zn^{2+}$.

Substituents that are useful cation chelating moieties include, e.g., heteroatom-containing groups including, e.g., nitrogen, oxygen, sulfur and phosphorous, attached to the heterocyclic core through a group that includes unsaturation (e.g., aryl, heteroaryl, alkenyl, and alkynyl). Useful cation chelating moieties include, e.g., amide, amidino, amine, aryl, arylalkyl, carbamate, carbonyl, carboxamido, carboxy, ether, heteroaryl, heterocyclyl, imino, nitro, phosphate, sulfate, sulfonamide, sulfonyl, sulfide, thiocarbonyl, and combinations thereof. Suitable chelating structures include, e.g., macrocycles, cryptands, crown ethers, azo crown ethers, thio crown ethers, and combinations thereof that include at least one Lewis basic site (e.g., oxygen, sulfur, nitrogen, phosphorous, and combinations thereof). Useful chelating structures include the following, where the structures are attached to the core at at least one of $R_1$, $R_2$, and $R_3$:

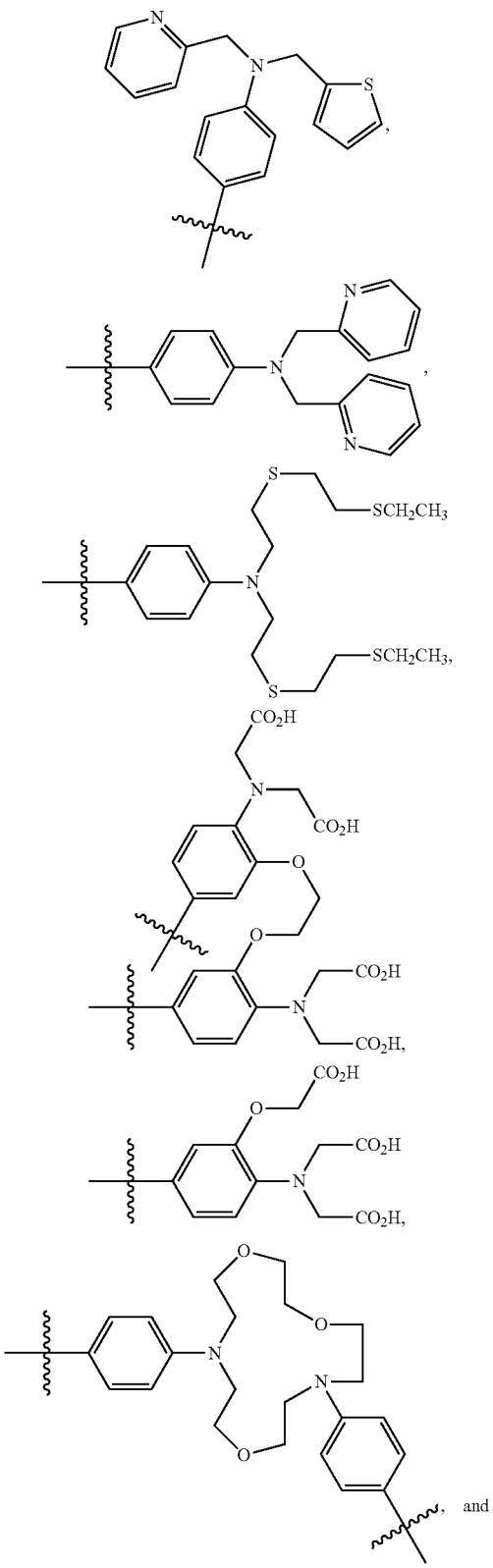

-continued

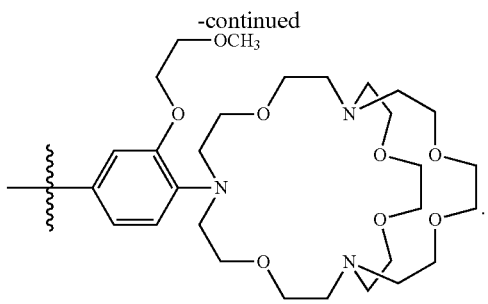

The cation chelating moiety can be selected to bind a variety of metal ions including the metal ions set forth above and incorporated herein.

The cation sensors can be used to detect a cation by contacting a sample with a cation sensor, exciting the sensor with radiation, and monitoring the fluorescence emitted by the sample.

Monitoring the fluorescence emitted by the sample can result in the detection of cations as indicated by an increase in the intensity of the emission, a decrease in the intensity of the emission, a change in the wavelength of emission, and combinations thereof.

A change in the fluorescence emitted by the sample can be correlated to at least one change in the system including, e.g., the binding of at least one cation to the compound, a change in the pH of the system, a change in the concentration of cation presence in the system, and combinations thereof.

The cation sensors also can be used to monitor intracellular ions (e.g., $Ca^{2+}$, $Mg^{2+}$, $Fe^{2+}$ and $Zn^{2+}$) in a cell. In one method, intracellular metal ions are detected in live cells.

Hydrophobicity Sensor

The substituents on the imidazo[1,5-a]pyridinium ion core of the compound of formula (II) can be selected to achieve a hydrophobicity sensor, i.e., a sensor that is capable of detecting a hydrophobic component. The hydrophobicity sensor can sense a variety of hydrophobic components including, e.g., hydrophobic environments (e.g., local hydrophobicity, i.e., the hydrophobicity surrounding the sensor), hydrophobic components of biological systems, and combinations thereof. Hydrophobic environments include, e.g., inorganic solvents (e.g., acetonitrile, hexane, benzene, toluene, tetrahydrofuran, chloroform, dichloromethane, dimethylsulfoxide), nonpolar buffers (e.g., sodiumdodecylsulfate), dendrimers, polymers, synthetic micelles, and can include hydrophobic components of biological systems. Hydrophobic components of biological systems include, e.g., cell membranes, lipid bilayers, micelles (e.g., natural micelles), and protein binding pockets.

The hydrophobicity sensor can be used in a variety of applications including, e.g., probing the location of a hydrophobic environment, probing the concentration of select analytes in immediate proximity to the sensor, monitoring the hydrophobicity of the environment surrounding the sensor, and optionally detecting at least one of the presence, absence, and concentration of a cation.

The hydrophobicity sensor can exhibit a variety of fluorescence responses to a hydrophobic component including, e.g., being free from fluorescence emission (e.g., exhibits fluorescence quenching) in the absence of a hydrophobic component and emitting fluorescence in the presence of hydrophobic component. The hydrophobicity sensor can additionally exhibit the cation sensor fluorescence responses set forth above with respect to cation sensors.

The mode in which the sensor functions depends upon the substituents on the imidazo[1,5-a]pyridinium ion core, the environment in which the sensor is located, the cations present in the environment, and combinations thereof. The substituents on the imidazo[1,5-a]pyridinium ion core can be selected to achieve a hydrophobicity sensor that functions as a turn-on hydrophobicity sensor, a ratiometric response cation sensor, and combinations thereof. The hydrophobicity sensor can function as a turn-on sensor, for example, in aqueous environments (e.g., water and water-based solvents), as a ratiometric response sensor in a nonpolar environment (e.g., an organic solvent), and combinations thereof. Alternatively, the hydrophobicity sensor can function as both a turn-on sensor and a ratiometric sensor in nonpolar environments. For some hydrophobicity sensors, the turn-on fluorescence emission is modulated by PET or ICT and the ratiometric response is modulated by a combination of ICT and PET.

One useful class of hydrophobicity sensors has a chemical structure according to the following formula

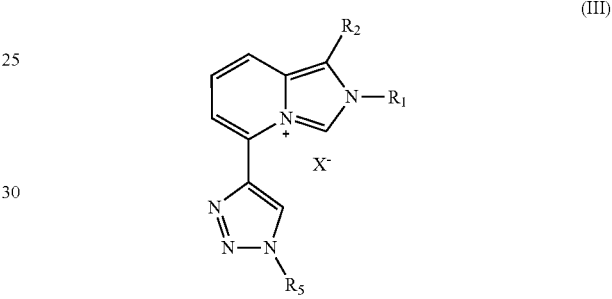

(III)

where $R_1$ is phenyl$C_{1-4}$ alkyl, phenyl$C_{1-4}$ alkoxy, phenylamine, phenyl(di-$C_{1-4}$ alkyl)amine, or phenylhalo$C_{1-4}$alkyl, $R_2$ is H, and $R_5$ is phenyl$C_{1-4}$ alkyl, phenyl$C_{1-4}$ alkoxy, phenylamine, phenyl(di-$C_{1-4}$ alkyl)amine, or phenylhalo-$C_{1-4}$alkyl, or even where $R_1$ is phenyl(di-$C_{1-4}$ alkyl)amine (e.g., 4-phenyldiethylamine), $R_2$ is H, and $R_5$ is phenyl$C_{1-4}$ alkyl or phenyl(di-$C_{1-4}$ alkyl)amine.

One example of a useful hydrophobicity sensor that exhibits turn-on hydrophobicity sensing and ratiometric cation sensing includes compounds of formula (III) in which $R_1$ is phenyldialkylamine (e.g., phenyldimethylamine and phenyldiethylamine), $R_2$ is H, and $R_5$ is phenylalkyl.

One example of a useful method of using the hydrophobicity sensor includes contacting a system with the hydrophobicity sensor and detecting a change in the fluorescence emission of the system. The change can be indicative of the presence or absence of a hydrophobic component, the presence or absence of a cation, and combinations thereof.

Additional Uses

The imidazo[1,5-a]pyridinium ions are suitable for a variety of uses including, e.g., as fluorescent labels, fluorogenic probes, and combinations thereof, and in a variety of methods including, e.g., methods of labeling, binding, quantitating, quantifying, monitoring, detecting, and screening biological species (e.g., biomolecules and biological structures). One useful method includes staining tissue with a imidazo[1,5-a]pyridinium ion disclosed herein. Biomolecules that can be labeled with the imidazo[1,5-a]pyridinium ions include, e.g., DNA, RNA, monosaccharides, polysaccharides, nucleotides (ATP, GTP, cAMP), lipids, peptides, and proteins (including enzymes and other structural proteins). The imidazo[1,5-a]pyridinium ions can also be used to label such biological structures as lipid bilayers, membranes, micelles, transmembrane proteins, ribosomes, liposomes, nucleosomes, peroxisomes, cytoskeletal units, plastids, chloroplasts, and mitochondria. Additionally, imidazo[1,5-a]pyridinium ions can be covalently attached to other small molecules known to bind specific biomolecule targets, allowing, for example, the sequence-specific labeling of DNA and RNA strands, the specific labeling of target proteins, and the localization of these probes in select regions of the cellular membrane.

The biomolecules and biological structures can interact with the imidazo[1,5-a]pyridinium ions or a moiety coupled to the ion in a variety of manners including, e.g., through a covalent bond, through an ionic bond, through a pi-pi stacking interaction, through hydrophobic interactions, through ampiphilic interactions, through van der Waals interactions, fluorophore-fluorophore interactions, and combinations thereof. The interaction can be reversible or irreversible. The interaction can be with the surface, an interior cavity, binding site, or other available structure or space of the biomolecules and biological structures.

The methods of use can further include visualizing the imidazo[1,5-a]pyridinium ion bound to the biomolecules. The visualization can be performed exposing the sample to radiation followed by a variety of techniques including, e.g., epifluorescence microscopy, total internal reflection fluorescence microscopy, confocal microscopy, two-photon or three-photon emission microscopy, second harmonic imaging microscopy, polarization microscopy, and aperture-based or apertureless near-field optical microscopy. The methods of use can further include quantifying the imidazo[1,5-a]pyridinium ion bound to the biomolecules. The quantification can be performed using a variety of techniques including, e.g., counting detected photons in a time interval, pumping the fluorophore with light of different polarizations, measuring the polarization of the detected photons, measuring the anisotropy of the detected photons, measuring the spectrum of the detected photons, measuring the lifetime of the detected photons, measuring the correlations of the detected photons, and combinations thereof. Correlations can be measured a variety of techniques including, e.g., fluorescence correlation spectroscopy, start-stop coincidence counting, using hardware autocorrelators, time-tagging the emission time of each photon with respect to the time of a pumping light pulse followed by off-line computation, and combinations thereof.

The imidazo[1,5-a]pyridinium ions can be provided neat or in the form of a composition that includes a carrier. Useful carriers include, e.g., solvents (aqueous solvents, organic solvents, and combinations thereof) buffers, and combinations thereof. The imidazo[1,5-a]pyridinium ions can also be packaged in any suitable packaging including, e.g., a kit. One useful package includes the imidazo[1,5-a]pyridinium ion, optionally in a carrier, disposed in a container (e.g., packet, vial, tube, and ampoule).

The invention will now be described by way of the following examples. All parts, ratios, percentages and amounts stated in the Examples are by weight unless otherwise specified.

EXAMPLES

Test Procedures

Test procedures used in the examples include the following. All ratios and percentages are by weight unless otherwise indicated. The procedures are conducted at room temperature (i.e., an ambient temperature of from about 20° C. to about 25° C.) unless otherwise specified.

Stock Solution Preparation

Stock solutions of each compound (having a concentration of from 1-5 mM) were prepared by dissolving the corresponding salts of the compounds in methanol or 1V, N-dimethylformamide, and then diluting the same with acetonitrile or buffered water having a pH of from 2.5 to 7.5 derived from 0.2 M sodium hypophosphate and 0.1 M citric acid, to achieve a sample solution having a compound concentration of 30.0 µM.

Method for Obtaining an Ultraviolet-Visible Light Spectrum

Ultraviolet-visible (UV-Vis) Light spectra are obtained and recorded on an Agilent 8453 spectrophotometer using ChemStation software (Agilent Technologies, Inc., Santa Clara, Calif.).

Method for Obtaining a Fluorescence Emission Spectrum

Fluorescence emission spectra are obtained and recorded on a QM-4-CW Spectrofluorometer using FeliX32 software (Photon Technology International, Inc., Birmingham, N.J.).

Method for Determining Quantum Yield

Quantum yield is determined using an integrating sphere attached to a QM-4-CW Spectrofluorometer using FeliX32 software (Photon Technology International).

Method for Determining $pK_a$

A $pK_a$ value is determined by plotting fluorescence intensity ($I_{max}$) at emission maxima against pH and fitting the result to the non-linear expression in equation (1) (i.e., eq.(1)). In eq (1), a and b are the molar coefficient of the acid (HA) and base (A$^-$) form, respectively, and c is the combined overall concentration of the acid and base form. i.e., c=[HA]+[A$^-$].

$$I_{max} = (a-b)\left(\frac{c*10^{(pKa-pH)}}{1+10^{(pKa-pH)}}\right) + (b*c) \quad (1)$$

Preparation of Starting Materials

Picolinaldehyde, N,N-diethylbenzene-1,4-diamine, n-butylamine and aniline were purified by short path vacuum distillation prior to use. Ethanol was dried over 3 Å molecular sieves. Solutions of 3 M hydrochloric acid in ethanol were generated by the addition of acetylchloride to dry ethanol in an ice bath, and standardized by titration with a known concentration of sodium hydroxide using phenolphthalein as an indicator. All other reagents were obtained from commercial sources and used without further purification unless otherwise noted.

General Procedure (A) for Preparing Imidazo[1,5-a]Pyridine Fluorophores:

Imidazo[1,5-a]pyridine fluorophores were prepared by adding 1 equivalent (equiv) of 3 M hydrochloric acid in ethanol (an additional equivalent of acid was used in reactions with basic substrates) and picolinaldehyde or other 2-acylpyridine to 1 equiv of a 0.5 M solution of 1 equiv of primary amine in dry ethanol or acetonitrile and 1.5 equiv of formalin. The reaction was stirred at room temperature for the specified period of time (i.e., from about 15 min to about 12 hours) and monitored by analytical thin layer chromatography (TLC) (10% methanol in DCM) for the appearance of a blue fluorescent product spot by UV light. Crude reaction mixtures were concentrated in vacuo (~15 Torr) and dried under high vacuum at 0.2 Torr (for from 2 to 12 hours).

Chloride salts were obtained through filtration of precipitate, recrystallization or trituration of the crude solid under conditions given. Hexafluorophosphate salts were obtained by salt metathesis with potassium hexafluorophosphate following the General Procedure for Salt Metathesis to Hexafluorophosphate Counterion. Tetraphenylborate salts were obtained by salt metathesis using sodium tetraphenylborate as described with respect to the compounds below that are in the form of tetraphenylborate salts.

General Procedure (B) for Preparing Imidazo[1,5-a]Pyridinium Ions:

To a 0.5 M solution of primary amine (1 equiv) in dry ethanol at room temperature is added paraformaldehyde (1.5 equiv). The resulting suspension is stirred at room temperature until the solution becomes homogeneous. One equivalent of 3 M hydrochloric acid in ethanol is then added to the solution followed by either picolinaldehyde or a 2-acylpyridine derivative (1 equiv). The reaction is stirred at room temperature for the amount of time specified (e.g., from 15 min to 4 days) and monitored by analytical TLC (10% methanol in DCM) for the appearance of a blue fluorescent product spot by UV light. Crude reaction mixtures were concentrated and placed under high vacuum (i.e., 0.2 Torr). Chloride salts were obtained through filtration of precipitate, recrystallization or trituration of the crude solid under conditions specific for the given substrate. Hexafluorophosphate salts were obtained by salt metathesis with potassium hexafluorophosphate following the General Procedure For Salt Metathesis to Hexafluorophosphate Counterion.

General Procedure for Salt Metathesis to Hexafluorophosphate Counterion:

Hexafluorophosphate salts were obtained by dissolving crude solids in a minimal amount of water followed by slow addition of concentrated aqueous potassium hexafluorophosphate ($KPF_6$) (1.1 equiv of $KPF_6$ per mol of imidazo[1,5-a]pyridinium salt) while stirring. The resulting precipitate was either filtered, in the case of a solid, or extracted with three portions of ethyl acetate in the case of a semi-solid. Solids collected by precipitation were confirmed to be analytically pure using $^1$H-NMR. Ethyl acetate layers from the extraction procedure were combined, washed once with water, dried over magnesium sulfate, filtered and concentrated. The resulting solids were triturated with diethyl ether, then filtered or decanted to obtain pure material.

General Procedure for Preparing Triazole Substituted Imidazo[1,5-a]Pyridinium Ions:

Triazoles substituted imidazo[1,5-a]pyridinium ions were prepared using a Huisgen Alkyne-Azide copper catalyzed cycloaddition reaction by adding 1 molar equivalent of 3 M hydrochloric acid in ethanol and 6-ethylyne-2-acylpyridine, to 1 molar equiv of a 0.5 M solution of primary amine in dry ethanol, methanol, or acetonitrile and 1.5 molar equiv of formalin. The reaction was stirred at room temperature for 16 hours and monitored by analytical thin layer chromatography (TLC) (10% methanol in DCM, UV-light visualization) or 1H NMR for completion of the imidazo[1,5-a] pyridinium ion forming reaction.

One molar equivalent of a substituted azide in 0.5 M solvent (e.g., ethanol, methanol or acetonitrile), and 1 mole % of a copper (Cu) (I) were then added to the reaction mixture and the reaction was allowed to proceed, with stirring, for 12 hours at room temperature.

Crude reaction mixtures were concentrated and placed under high vacuum (i.e., 0.2 Torr). Chloride salts were obtained through filtration of precipitate, recrystallization or trituration of the crude solid under conditions specific for the given substrate. Hexafluorophosphate salts were obtained by salt metathesis with potassium hexafluorophosphate following the General Procedure for Salt Metathesis to hexafluorophosphate counterion.

Comparative Example

2-Butylimidazo[1,5-a]pyridinium hexafluorophosphate

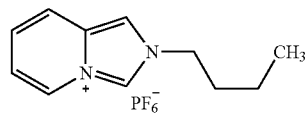

was prepared according to General Procedure (A), in which 0.31 mL n-butylamine (3.1 mmol, 1 equiv), 0.35 mL formalin (4.7 mmol, 1.5 equiv), 1.1 mL 2.94 M hydrochloric acid in ethanol (3.1 mmol, 1 equiv) and 0.30 mL picolinaldehyde (3.1 mmol, 1 equiv) were combined in 5.2 mL ethanol and maintained at room temperature for 4 hours. Salt metathesis with $KPF_6$ resulted in a semi-solid, which upon extraction with ethyl acetate (3 three times using 10 mL of ethyl acetate each time) and trituration with 6.0 mL diethyl ether, yielded 0.86 g 2-butylimidazo[1,5-a]pyridinium hexafluorophosphate (2.7 mmol, a 86% yield) as a white solid.

Example 1: Compound 1

Compound 1, i.e., 2-(4-(diethylamino)phenyl)-5-ethynyl-2H-imidazo[1,5-a]pyridin-4-ium chloride,

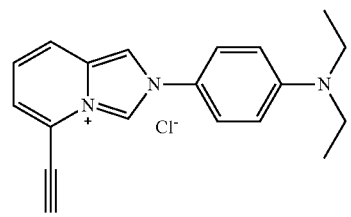 [SMILES: C#Cc1cccc2cn(-c3ccc(N(CC)CC)cc3)c[n+]12 ; [Cl-]]

was prepared according to the General Procedure General Procedure (A) For Preparing Imidazo[1,5-a]pyridine Fluorophores: where the picolinaldehyde was 2-ethynyl picolinaldehyde, and the primary amine was $N^1,N^1$-diethylbenzene-1,4-diamine. The procedure was modified from the general procedure by using the bis-hydrochloric acid salt of the amine instead of 3 M hydrochloric acid in ethanol. The workup was modified by dissolving crude material in an acetonitrile ethanol mixture (2:1) and stirring with an excess of solid sodium bicarbonate to remove excess acid. The bicarbonate was removed by filtration through a 0.2 μm nylon syringe tip filter.

Example 2: Compound 2

2-(4-(diethylamino)phenyl)-2H-imidazo[1,5-a]pyridin-4-ium hexafluorophosphate (9)

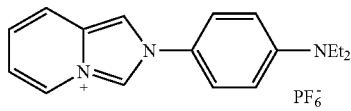

was prepared according to general procedure (A) in which a reaction mixture was prepared by combining 186 μl ethanol formalin (2.48 mmol, 1.5 equiv) and freshly distilled 274.6

µl N,N-diethylbenzene-1,4-diamine (1.66 mmol, 1 equiv). Then, 158 µl picolinaldehyde (1.66 mmol, 1 equiv) and 1.09 µl 3.14 M hydrochloric acid in ethanol (3.31 mmol, 2 equiv) were simultaneously added to the reaction mixture and the reaction was maintained at room temperature for 12 hours. The solution was concentrated and the crude chloride salt subjected to salt metathesis with potassium hexafluorophosphate. The resulting precipitate was filtered and washed with water two times using 500 µl of water for each wash. The precipitate was then dried under high vacuum at 0.2 Torr, dissolved in 5 mL acetonitrile, and stirred with 800 mg sodium bicarbonate for 30 minutes at room temperature. The resulting suspension was filtered through a 0.2 µm nylon syringe tip filter and concentrated in vacuo to provide 509 mg 2-(4-(diethylamino)phenyl)-2H-imidazo[1,5-a]pyridin-4-ium hexafluorophosphate (1.24 mmol, at a 74.7% yield) as red solid. Crystals suitable for X-ray diffraction were obtained by layering a concentrated acetone solution of 2-(4-(diethylamino)phenyl)-2H-imidazo[1,5-a]pyridin-4-ium hexafluorophosphate with pentane.

Example 3: Compound 3

2-butyl-1-(p-tolyl)-2H-imidazo[1,5-a]pyridin-4-ium tertraphenylborate

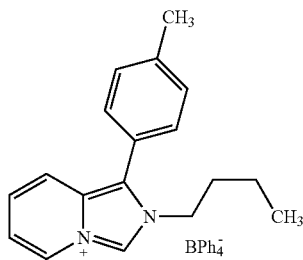

was prepared according to general procedure (A), in which 25 µl n-butylamine (0.25 mmol, 1 equiv), 28 µl formalin (0.37 mmol, 1.5 equiv), 82 µl 3.05 M hydrochloric acid in ethanol (0.25 mmol, 1 equiv) and 49 mg pyridin-2-yl(p-tolyl)methanone (0.25 mmol, 1 equiv) were combined in 0.50 mL acetonitrile and maintained at room temperature for 12 hours. The crude material was then dissolved in 1.0 mL methanol and then 94 mg sodium tetraphenylborate (0.27 mmol, 1.1 equiv) in 1.0 mL methanol was added drop wise while stirring vigorously. The heterogeneous mixture was stirred vigorously for 3 hours at room temperature until the solid became a fine suspension, which was then filtered, washed with 500 µl of methanol and dried under high vacuum at 0.2 Torr to obtain 105 mg 2-butyl-1-(p-tolyl)-2H-imidazo[1,5-a]pyridin-4-ium tetraphenylborate (0.18 mmol, a 72% yield) as a white solid.

Example 4: Compound 4

2-butyl-1-(4-methoxyphenyl)-2H-imidazo[1,5-a]pyridin-4-ium chloride

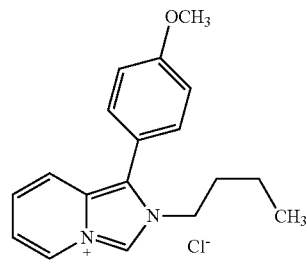

was prepared according to general procedure (A, in which 35 µl n-butylamine (0.35 mmol, 1 equiv), 40 µl formalin (0.53 mmol, 1.5 equiv), 0.11 mL 3.14 M hydrochloric acid in ethanol (0.35 mmol, 1 equiv) and 76 mg (4-methoxyphenyl)(pyridin-2-yl)methanone (0.35 mmol, 1 equiv) were combined in 0.70 mL acetonitrile and maintained at room temperature for 12 hours. The crude material was then dissolved in 3 mL ethanol and stirred with sodium bicarbonate at room temperature for 10 min. The resulting suspension was then filtered through a 1.0 mL 0.2 um nylon syringe tip filter and the solid was rinsed with an additional 1 mL of ethanol. The combined filtrate was then concentrated and triturated with 2 mL diethyl ether. The resulting solid was filtered and rinsed with diethyl ether two times using 1 mL of diethyl ether for each rinse providing 0.10 g 2-butyl-1-(4-methoxyphenyl)-2H-imidazo[1,5-a]pyridin-4-ium chloride (0.23 mmol, a 66% yield) as a white solid.

Example 5: Compound 5

2-butyl-1-(4-(diethylamino)phenyl)-2H-imidazo[1,5-a]pyridin-4-ium tetraphenylborate

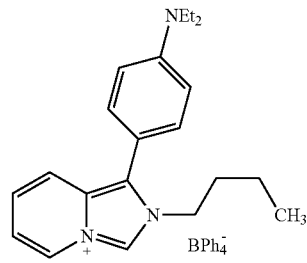

was prepared according to general procedure (A), in which 25 µl n-butylamine (0.21 mmol, 1 equiv), 24 µl formalin (0.32 mmol, 1.5 equiv), 0.14 mL 3.05 M hydrochloric acid in ethanol (0.43 mmol, 2 equiv) and 54 mg (4-(diethylamino)phenyl)(pyridin-2-yl)methanone (0.21 mmol, 1 equiv) were combined in 1.0 mL acetonitrile and maintained at room temperature for 12 hours. The reaction was concentrated in vacuo and dried under high vacuum at 0.2 Torr. The resulting crude material was dissolved in 1.5 mL ethanol and stirred with 0.8 g sodium bicarbonate for 1 hour at room temperature. The resulting suspension was then filtered through a 0.2 um nylon syringe tip filter, washed with ethanol three times using 6 mL of ethanol for each wash and filtered. The combined filtrate was concentrated. The resulting crude oil was dissolved in 1.5 mL methanol and 73 mg sodium tetraphenylborate (0.21 mmol, 1 equiv) in 1.5 mL methanol was added drop wise to the oil while stirring vigorously. The heterogeneous mixture was stirred vigorously for 3 hours at room temperature until the solid became a fine suspension. The mixture was cooled to 4° C. in a refrigerator. The solid was then filtered, rinsed with methanol three times using 0.25 mL of methanol for each rinse and dried under high vacuum at 0.2 Torr to obtain 96 mg 2-butyl-1-(4-(diethylamino)phenyl)-2H-imidazo[1,5-a]pyridin-4-ium tetraphenylborate (0.15 mmol, a 70% yield) as an orange solid.

The photophysical properties of compounds 1-5 were determined. The compounds included hydrogen at each position that is not otherwise specified: the positions that are specified are specified with reference to the following structure:

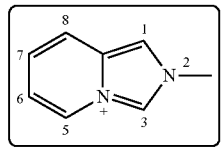

The compounds were analyzed at 298° K according to the Method for Obtaining Ultraviolet-Visible Light Spectrum (30 μM acetonitrile) to obtain the maximum absorbance wavelength ($\lambda_{abs,max}$), Method for Obtaining Fluorescence Emission Spectrum (30 μM acetonitrile) to obtain the maximum emission wavelength ($\lambda_{em,max}$) and Method for Determining Quantum Yield ($\Phi_F$) (30 μM acetonitrile) at the concentration, in the solvent, and with the counter ion indicated in Table 1. The compounds included hydrogen at each R group that is not otherwise specified.

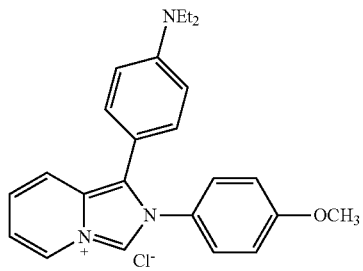

was prepared according to general procedure (A), in which 28 μg 4-methoxyaniline (0.22 mmol, 1 equiv), 24 μl formalin (0.34 mmol, 1.5 equiv), 0.14 mL 3.14 M hydrochloric acid in ethanol (0.45 mmol, 2 equiv) and 57 mg (4-(diethylamino)phenyl)(pyridin-2-yl)methanone (0.22 mmol, 1 equiv) were combined in 0.45 mL ethanol and maintained at room temperature for 12 hours. The reaction was concentrated in vacuo and dried under high vacuum at 0.2 Torr. The crude material was triturated with 1.5 mL acetone, which resulted in the formation of a solid. The suspension was then filtered and rinsed with (2:1) acetone/diethylether three times using 1 mL of (2:1) acetone/diethylether for each rinse. The resulting solid was dried under high vacuum at 0.2 Torr for 48 hours to provide 80 mg 1-(4-(diethylamino)phenyl)-2-(4-methoxyphenyl)-2H-imidazo[1,5-a]pyridin-4-ium chloride (0.18 mmol, a 80% yield) as a cream colored solid. This material was determined to be the monocationic salt by titration with sodium hydroxide.

TABLE 1

| Compound | Position of Group 1 | Group 1 | Position of Group 2 | Group 2 | Counter Ion | $\Phi_F$ % | $\lambda_{abs,max}$ Abs (nm) | $\lambda_{em,max}$ Em (nm) |
|---|---|---|---|---|---|---|---|---|
| 2 | NA | NA | 2 | —⟨⟩—N(CH₂CH₃)₂ | PF₆⁻ | 30 | 330 | 515 |
| 3 | 2 | n-Bu | 1 | —⟨⟩—CH₃ | TFB | 46 | 320 | 415 |
| 4 | 2 | n-Bu | 1 | —⟨⟩—OCH₃ | Cl⁻ | 64 | 320 | 430 |
| 5 | 2 | n-Bu | 1 | —⟨⟩—N(CH₂CH₃)₂ | TFB | 38 | 355 | 550 | n-Bu = n-butyl
TFB = tetraphenylborate
a = this compound exhibited a broad emission and with multiple vibronic features.

Example 6: Compound 6

1-(4-(diethylamino)phenyl)-2-(4-methoxyphenyl)-2H-imidazo[1,5-a]pyridin-4-ium chloride Example 7: Compound 7

Compound 7, i.e., 2-(4-(diethylamino)phenyl)-1-(4-methoxyphenyl)-2H-imidazo[1,5-a]pyridin-4-ium chloride

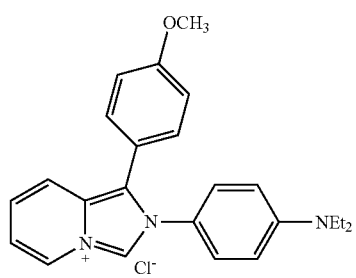

was prepared according to general procedure (A), in which freshly distilled 0.12 μl N,N-diethylbenzene-1,4-diamine (0.74 mmol, 1 equiv), 83 μl formalin (0.1.1 mmol, 1.5 equiv), 0.47 mL 3.14 M hydrochloric acid in ethanol (1.5 mmol, 2 equiv) and 0.16 g (4-methoxyphenyl)(pyridin-2-yl) methanone, (0.74 mmol, 1 equiv) were combined in 1.5 mL acetonitrile and maintained at room temperature for 12 hours. The reaction was concentrated in vacuo and dried under high vacuum at 0.2 Torr. The crude material was then triturated with 1.0 mL acetone and diluted with 0.5 mL diethylether. The resulting solution was decanted and the process was repeated an additional two times. The resulting solid was then dissolved in methanol, transferred to a tared vial, concentrated under a stream of nitrogen, and dried under high vacuum at 0.2 Torr for 48 hours to provide 0.27 g, 2-(4-(diethylamino)phenyl)-1-(4-methoxyphenyl)-2H-imidazo[1,5-a]pyridin-4-ium chloride (0.66 mmol, a 90% yield) as a deliquescent cream colored solid. This material was determined to be the monocationic salt by titration with sodium hydroxide. The material used for fluorescence testing was further purified by recrystallization from acetonitrile and tetrahydrofuran. Crystals used for X-ray diffraction were obtained by layering a concentrated methanolic solution of 2-(4-(diethylamino)phenyl)-1-(4-methoxyphenyl)-2H-imidazo[1,5-a]pyridin-4-ium chloride with pentane.

Example 8: Compound 8

2-(4-(dimethylamino)-2,6-diisopropylphenyl)-2H-imidazo[1,5-a]pyridin-4-ium tetraphenylborate

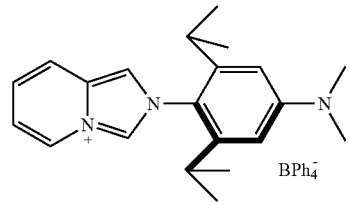

was prepared according to general procedure (A); 77 μg 3,5-diisopropyl-N,N-dimethylbenzene-1,4-diamine (0.35 mmol, 1 equiv), 39 μl formalin (0.53 mmol, 1.5 equiv), 0.23 mL 3.05 M hydrochloric acid in ethanol (0.70 mmol, 2 equiv) and 34 μl picolinaldehyde (0.35 mmol, 1 equiv) were combined in 1.8 mL ethanol and maintained at room temperature for 12 hours. The reaction was concentrated in vacuo and dried under high vacuum at 0.2 Torr. The crude material was then dissolved in 2.5 mL ethanol and stirred with 0.8 g sodium bicarbonate for 30 minutes at room temperature. The resulting suspension was then filtered through a 0.2 um nylon syringe tip filter. The solid sodium bicarbonate was washed with ethanol three times using 0.5 mL of ethanol for each wash and filtered. The combined filtrate was concentrated. The resulting crude oil was dissolved in 3.0 mL methanol and 0.12 g sodium tetraphenylborate (0.35 mmol, 1 equiv) in 1.0 mL methanol was added drop wise while stirring vigorously. The mixture was cooled to 4° C. in a refrigerator. The methanol was then decanted, and the solid was rinsed with methanol three times using 0.25 mL of methanol for each rinse and dried under high vacuum at 0.2 Torr to obtain 0.16 g 2-(4-(dimethylamino)-2,6-diisopropylphenyl)-2H-imidazo[1,5-a]pyridin-4-ium tetraphenylborate (0.26 mmol, a 73% yield) as a dark brown solid.

Example 9

A 30 μM solution of Compound 6 in acetonitrile was prepared by adding 99 μL of a stock solution of 3.04 mM Compound 6 in methanol to 10 mL of acetonitrile. An initial fluorescence emission spectrum of the solution was obtained and is illustrated by curve (i) in FIG. 1A.

A series of approximately 13.8 μL aliquots of trifluoroacetic acid (TFA) were then added to the 30 μM solution of Compound 6 until a total concentration of 60.0 mM of TFA was present in the solution. (The total amount of TFA present in the solution corresponded to 2000 equivalents of acid per equivalent of Compound 6.) The fluorescence emission spectrum of the resulting solution was obtained and is illustrated by curve (ii) in FIG. 1A. Compound 6 was observed to exhibit an increase in the emission intensity at $\lambda_{em,max}$=405 nm and a decrease in emission intensity at $\lambda_{em,max}$=565 nm as the amount of acid in the system increased.

A base, i.e., 1,8-diazabicyclo[5.4.0]undec-7-ene (DBU), was then added to the solution to neutralize the acid until a concentration of 90 mM DBU was obtained. The fluorescence emission spectrum of the resulting solution was obtained and is illustrated by curve (iii) in FIG. 1A. The fluorescence emission intensity at $\lambda_{em,max}$=565 nm increased as the amount of base present in the system increased and the fluorescence emission intensity at $\lambda_{em,max}$=405 nm decreased as the amount of base present in the system increased, which reflected Compound 6's ratiometric response to the changing base concentration in acetonitrile.

Example 10

A 30 μM solution of Compound 7 in acetonitrile was prepared by adding 84 μL of a stock solution of 3.58 mM Compound 7 in methanol to 10 mL of acetonitrile. The emission spectrum of the solution was then obtained and is illustrated by curve (i) in FIG. 1B. Compound 7 was essentially non-emissive in the acetonitrile (i.e., Compound 7 exhibited a quantum yield ($\Phi_F$)=0.06% when exited at 340 nm).

A series of approximately 13.8 μL aliquots of TFA were then added to the 30 μM solution of Compound 7 until a total concentration of 60.0 mM TFA was present in the solution (which corresponded to 2000 equivalents of acid per equivalent of Compound 7). The fluorescence emission spectrum of the solution was obtained and is illustrated by curve (ii) in FIG. 1B. The solution exhibited an approximately 700-fold increase in cyan fluorescent intensity, i.e., Compound 7 exhibited a maximum fluorescence emission $\lambda_{em,max}$ at 450 nm and an intensity of $\Phi_F$=42%. Compound 7 thus exhibited a turn-on signaling function when acid was present in the solution and a turn-off signaling function in neat acetonitrile.

After the 60 mM TFA concentration was achieved, DBU was gradually added to the solution until a total concentration of 90 mM DBU was present in the solution. The fluorescence spectrum of the solution was obtained and is illustrated by curve (iii) in FIG. 1B. The fluorescence intensity emission returned to zero.

Example 11

Figure 2A:
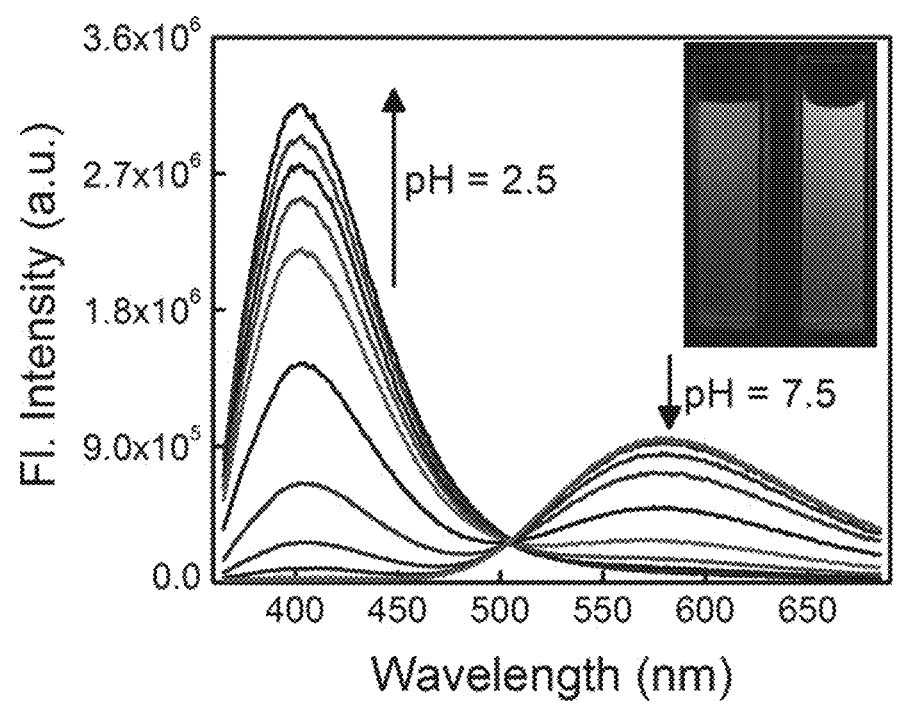
FIG. 2A is a plot of the fluorescence emission spectrum of 30 μM Compound 6 in a series of buffered water solutions having a pH of from 2.5 to 7.5.

A series of eleven samples were prepared by adding Compound 6 to a series of vessels that included buffered water at 298 K. The water in each vessel had a different pH such that the pH of each sample ranged from 2.5 to 7.5. The emission spectrum for each sample was obtained. The results are illustrated by the plot in FIG. 2A. Compound 6 was observed to exhibit an increase in the emission intensity at $\lambda_{em,max}$=400 nm and a decrease in emission intensity at $\lambda_{em,max}$=580 nm as the pH of the system decreased from 7.5 to 2.5, which reflects Compound 6's ratiometric response to changing pH in water.

Example 12

Figure 2B:
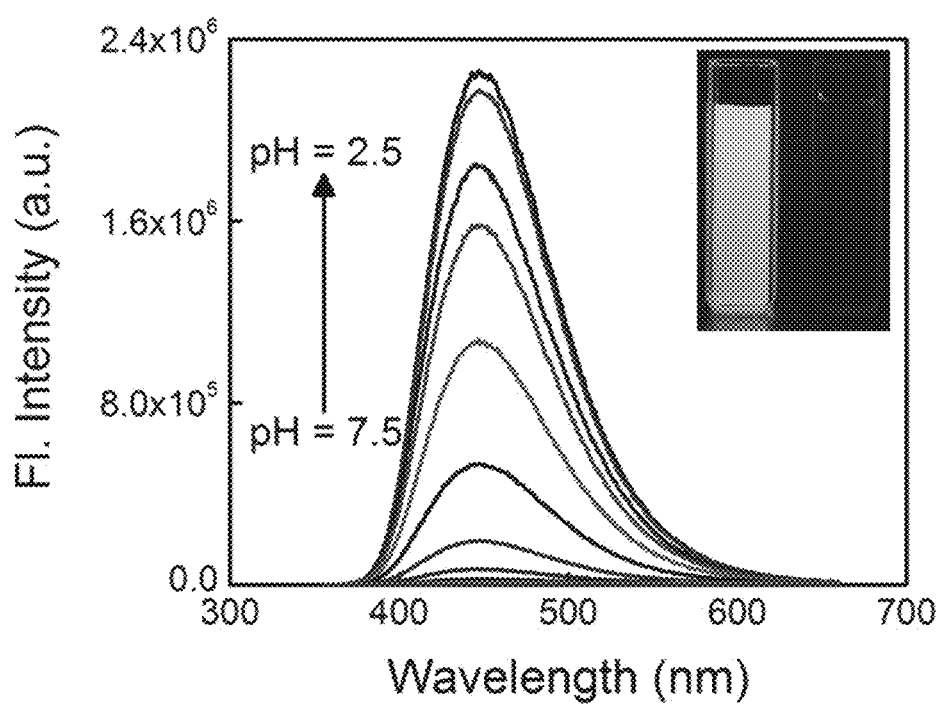
FIG. 2B is a plot of the fluorescence emission spectrum of 30 μM Compound 7 in a series of buffered water solutions having a pH of from 2.5 to 7.5.

A series of eleven samples were prepared by adding Compound 7 to a series of vessels that included buffered water at 298 K. The water in each vessel had a different pH such that the pH of the samples ranged from 2.5 to 7.5. The emission spectrum for each sample was obtained. Compound 7 was essentially non-emissive at pH 7.5 in water, but exhibited an increase in emission intensity at $\lambda_{em,max}$=450 nm as the pH of the system decreased from 7.5 to 2.5, which reflects Compound 7's turn-on response to changing pH in water. The results are illustrated in the plot of FIG. 2B.

Figure 3A:
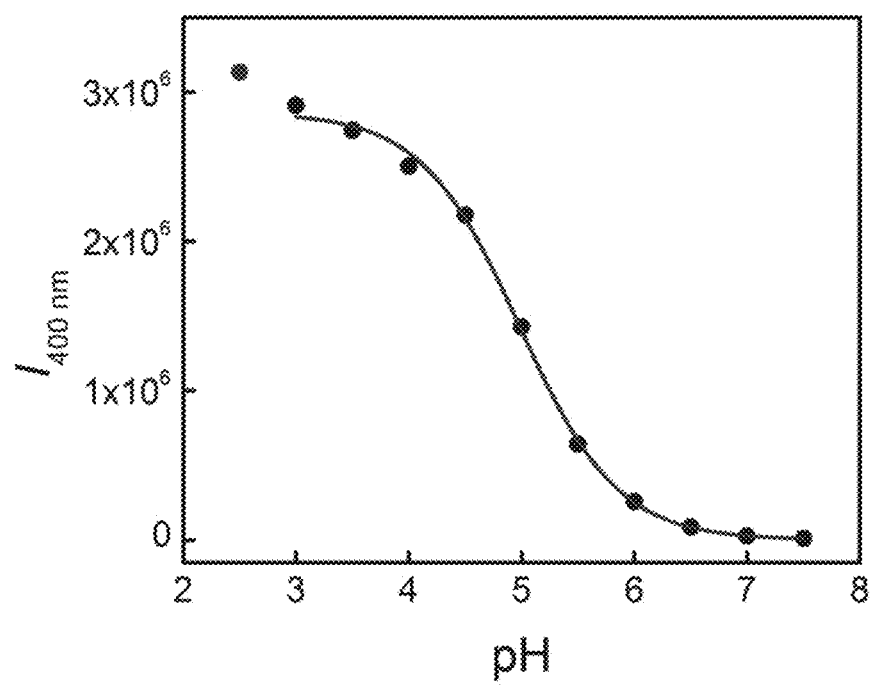
FIG. 3A is a plot of fluorescence intensity of Compound 6 at 400 nm versus pH.
Figure 3B:
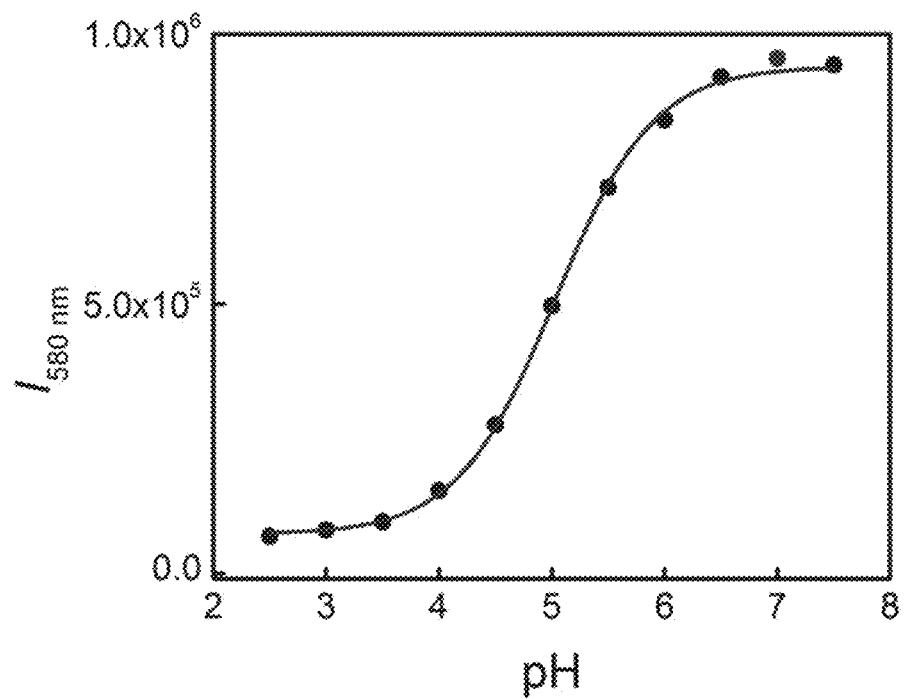
FIG. 3B is a plot of fluorescence intensity of Compound 6 at 580 nm versus pH.

The sigmoidal response of fluorescence intensity of Compound 6 at 400 nm versus pH and at 580 nm versus pH is illustrated by the plot in FIGS. 3A and 3B.

Figure 4:
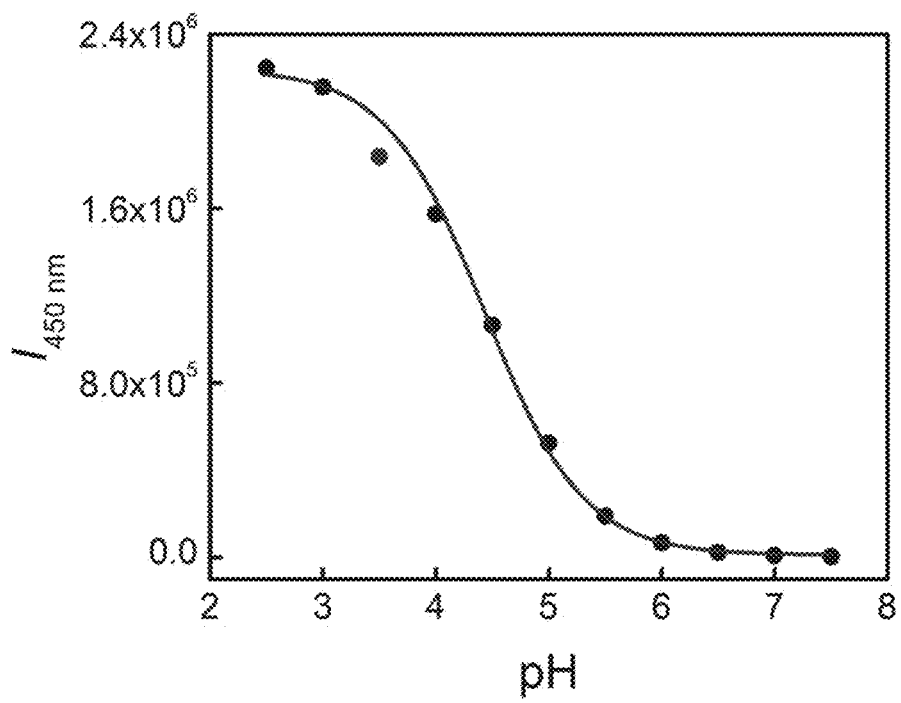
FIG. 4 is a plot of fluorescence intensity of 30 μM Compound 7 at 450 nm versus pH.

The sigmoidal response of fluorescence intensity of Compound 7 at 400 nm versus pH illustrated by the plot in FIG. 4

Non-linear regression of the sigmoidal response of fluorescence intensity versus pH was calculated according to the formula Method for Determining $pK_a$ and provided a $pK_a$=5.0 for Compound 6 and $pK_a$=4.4 for Compound 7.

Example 13A

Figure 5A:
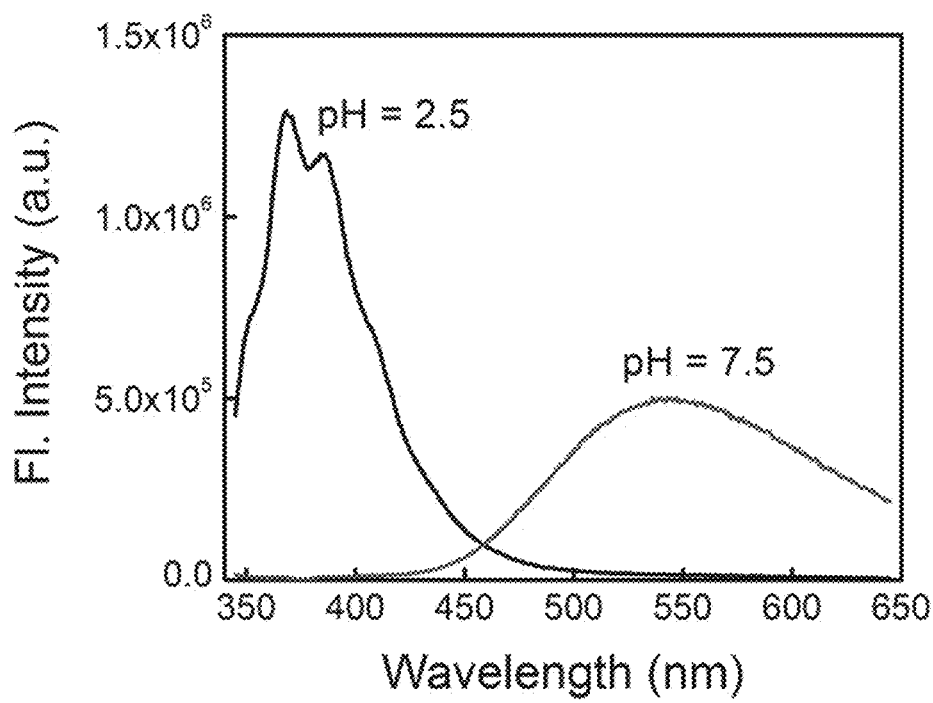
FIG. 5A is a plot of the fluorescence emission spectrum of 10 μM Compound 2 in water having a pH of 7.5 and in water having a pH of 2.5.

The fluorescence emission spectrum of 10 µM Compound 2 in water having a pH of 7.5 was obtained and demonstrated that Compound 2 exhibited an emission maxima at $\lambda_{em}$=550 nm at pH=7.5 in water, as illustrated by the flatter curved line in FIG. 5A. The pH of the system was subsequently decreased to pH=2.5 and Compound 2 exhibited strong fluorescence at $\lambda_{em}$=360-375 nm.

Figure 5B:
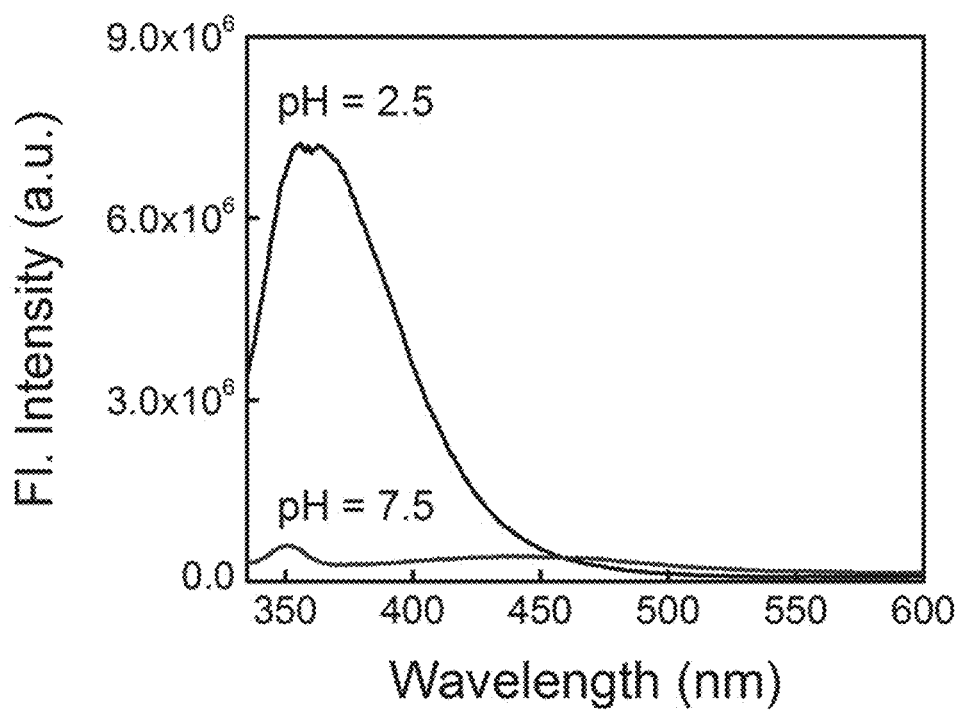
FIG. 5B is a plot of the fluorescence emission spectrum of 5 μM Compound 8 in water having a pH of 7.5 and in water having a pH of 2.5.

The fluorescence emission spectrum of 5 µM Compound 8 in water having a pH of 7.5 was obtained and is illustrated by the generally flat line in FIG. 5B, which demonstrates that Compound 8 exhibited fluorescence quenching in water having a pH of 7.5. The fluorescence emission spectrum of Compound 8 in water having a pH of 2.5 was also obtained and is illustrated by the curved line with a peak at 360 nm in FIG. 5B. Compound 8 exhibited an increase in emission intensity at $\lambda_{em,max}$=360 nm in an acidic environment.

This demonstrates the ICT-type emission of Compound 2 and PET-type relaxation of Compound 8, which can be controlled reversibly by straightforward acid-base chemistry.

Example 13B

Figure 6A:
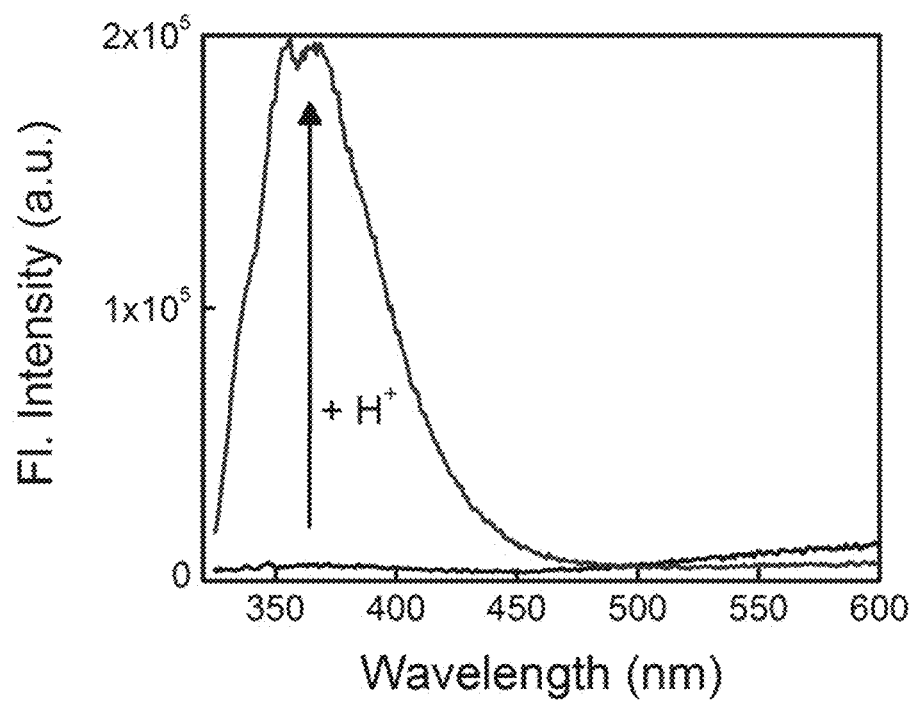
FIG. 6A is a plot of the fluorescence emission of Compound 8 in neat acetonitrile.

The fluorescence emission spectrum of Compound 8 in neat acetonitrile was obtained and is illustrated by the generally flat line in FIG. 6A, which demonstrates that Compound 8 exhibited fluorescence quenching in neat acetonitrile. An aliquot of 50 µL of trifluoroacetic acid was then added to the system, and the fluorescence emission spectrum was obtained and is illustrated by the curved line with a peak at 360 nm in FIG. 6A. Compound 8 exhibited an increase in emission intensity at $\lambda$em,max=360 nm in an acidic environment in acetonitrile.

Figure 6B:
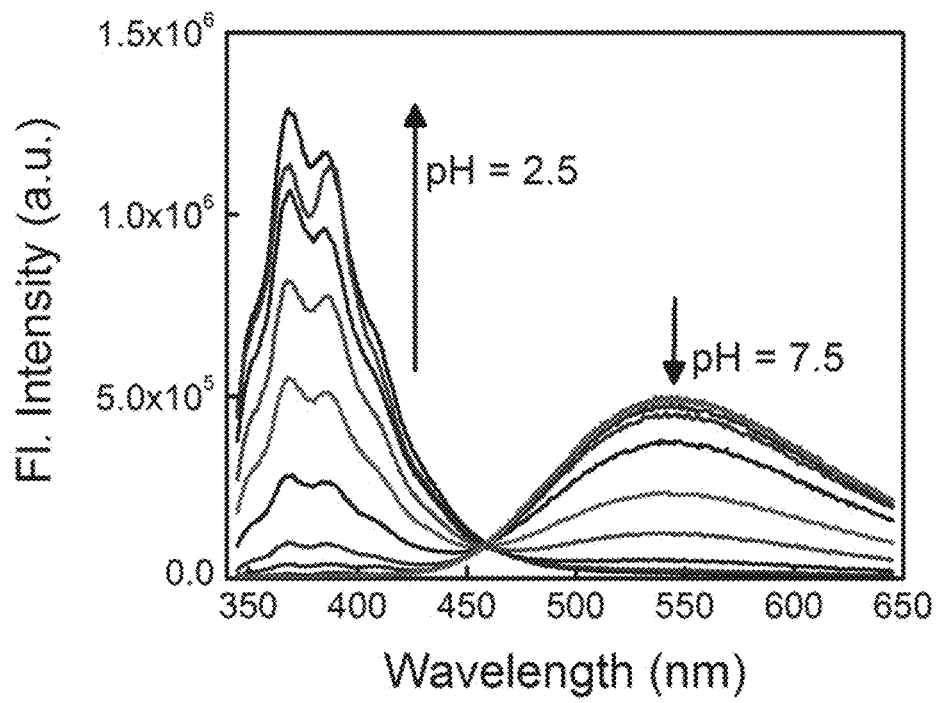
FIG. 6B is a plot of the fluorescence emission of Compound 2 in water.

The fluorescence emission spectrum of Compound 2 in neat acetonitrile having a pH of 7.5 was obtained and demonstrated that Compound 2 exhibited an emission maxima at $\lambda_{em}$=550 nm at pH=7.5 in water, as illustrated by the flatter curved line in FIG. 6B. The pH of the system was subsequently decreased to pH=2.5 and Compound 2 exhibited strong fluorescence at $\lambda_{em}$=360-375 nm.

Example 14

Compound 6 was placed in the series of organic solvents at a concentration of 30 µM, excited with radiation at 360 nm, and monitored for fluorescence emission. The organic solvent, intensity of fluorescence emission (ET), and maximum emission wavelength in nm and cm$^{-1}$, are set forth below in Table 2.

TABLE 2

| Solvent | ET(30) | Wavelength(nm) | wavenumber(cm$^{-1}$) |
|---|---|---|---|
| Hexane | 31 | 561 | 17825.31 |
| Benzene | 34.3 | 567 | 17636.68 |
| Toluene | 33.9 | 568 | 17605.63 |
| Tetrahydrofuran | 37.4 | 541 | 18484.29 |
| Chloroform | 39.1 | 533 | 18761.73 |
| Dichloromethane | 40.7 | 535 | 18691.59 |
| Acetonitrile | 45.6 | 559 | 17889.09 |
| Dimethylsulfoxide | 45.1 | 567 | 17636.68 |
| Water | 63.1 | 576 | 17361.11 |

Example 15: Compound 9

Compound 9, i.e., 2-butyl-5-(4-(dimethylamino)phenyl)-2H-imidazo[1,5-a]pyridin-4-ium tetraphenylborate

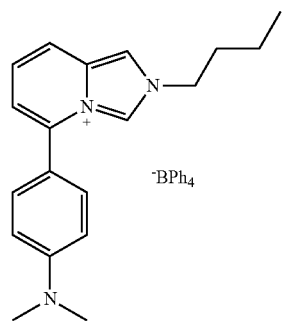

was prepared according to General Procedure (A) For Preparing Imidazo[1,5-a]pyridine Fluorophores: where the picolinaldehyde was 6-(4-(dimethylamino)phenyl) picolinaldehyde, and the primary amine was butylamine. The procedure was modified from the general procedure by using by using two equivalents of 3 M hydrochloric acid in ethanol, as well as by running the reaction in an ethanol:chloroform mixture (1:1). The workup was modified by dissolving the crude material in an acetonitrile ethanol mixture (2:1) and stirring with an excess of solid sodium bicarbonate to remove excess acid. The bicarbonate was removed by filtration through a 0.2 μm nylon syringe tip filter. The tetraphenylborate salt was obtained by following through salt metathesis with sodium tetraphenylborate following the general procedure.

Example 16: Compound 10

Compound 10, i.e., 5-(1-(4-(diethylamino)phenyl)-1H-1,2,3-triazol-4-yl)-2-(4-(dimethylamino)phenyl)-2H-imidazo[1,5-a]pyridin-4-ium chloride

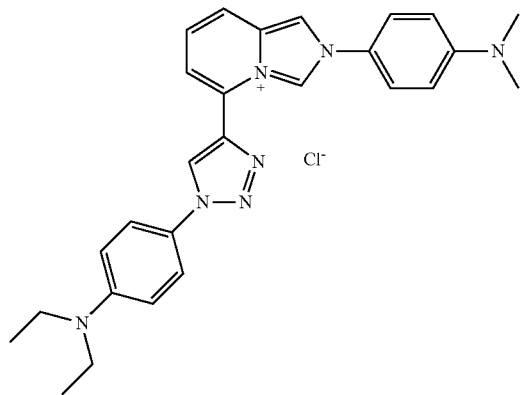

was prepared according to the General Procedure For Preparing Imidazo[1,5-a]pyridine Triazole Compounds: where the azide was 4-azido-N,N-diethylaniline, the amine was $N^1,N^1$-dimethylbenzene-1,4-diamine, and the copper source was copper (I) bromide dimethyl sulfide. The procedure was modified from the general procedure by using the bis-hydrochloric acid salt of the amine instead of 3 M hydrochloric acid in ethanol. The procedure was further modified by addition one equivalent of sodium hydroxide at the time of azide and copper addition.

Figure 7A:
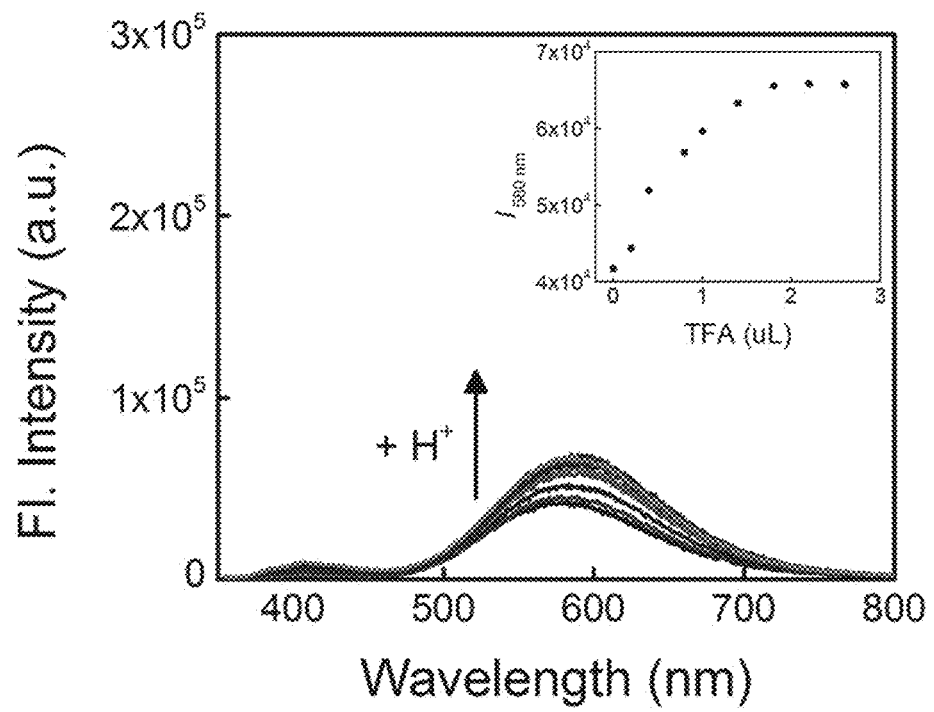
FIG. 7A is a plot of the fluorescence emission spectrum of Compound 10 in neat acetonitrile and with incrementally increasing amounts of trifluoroacetic acid.

Compound 10 was placed in neat acetonitrile and its emission spectrum was monitored as trifluoroacetic acid was added to the acetonitrile in incremental amounts to achieve a solution that included an acid concentration ranging from 0 to 0.2 M. After each acid addition the sample was excited with radiation of a wavelength 340 nm, and its fluorescence emission spectrum was monitored. The results are illustrated in FIG. 7A.

Figure 7B:
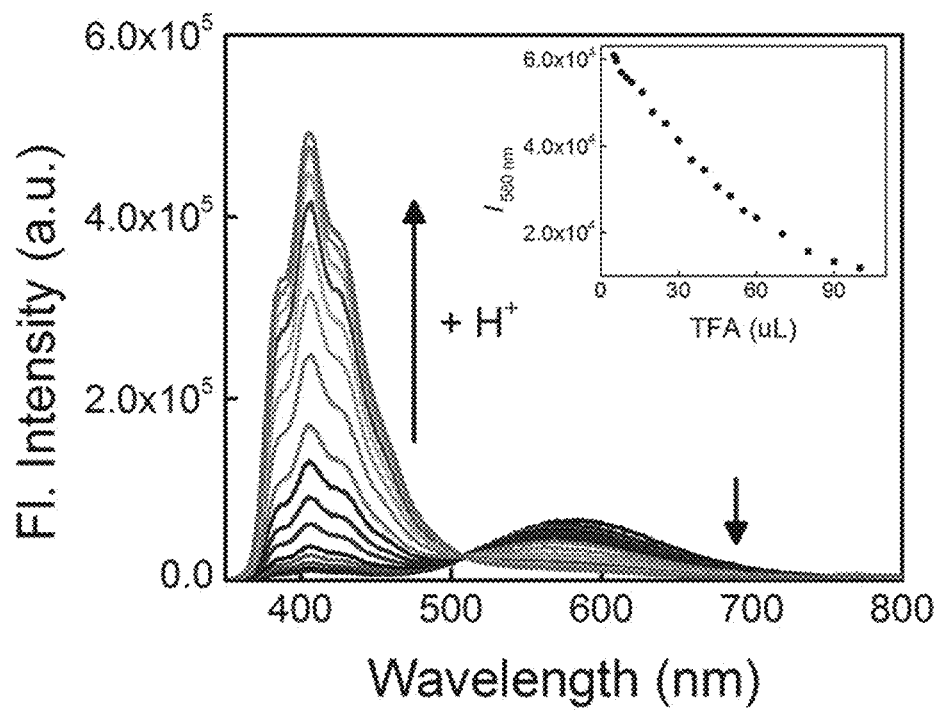
FIG. 7B is a plot of the fluorescence emission spectrum of Compound 10 in acetonitrile with increasing pH.
Figure 7C:
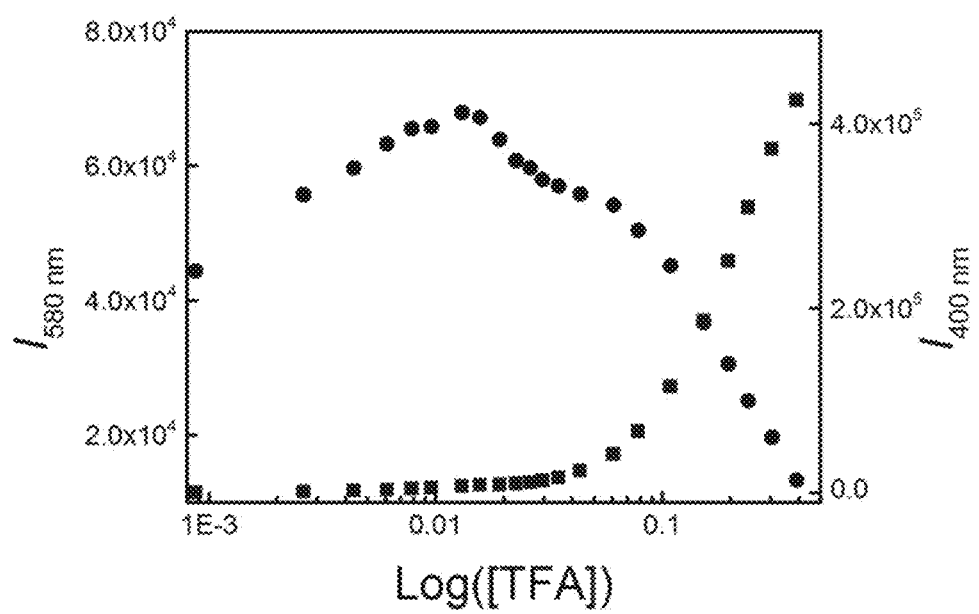
FIG. 7C is a plot of the emission intensity of Compound 10 at 580 nm (left ordinate) versus the log of the volume of trifluoroacetic acid in μL and at 400 nm (right ordinate) versus the log of the volume of trifluoroacetic acid in 4.

The solution of Compound 10 in acetonitrile was titrated with trifluoroacetic acid (TFA). The stepwise addition of TFA showed two stage transitions. The first stage, which occurred with the addition of the initial aliquots of TFA, was a slight increase intensity at 580 nm, as illustrated in FIG. 7A. As more TFA was added to the system, a second transition occurred in which the emission at 580 nm began to decrease and as the emission at 400 nm began to increase, as illustrated in FIG. 7B. A plot of the emission intensity at 580 nm versus pH and at 400 nm versus pH is illustrated in FIG. 7C.

Example 17: Compound 11

Compound 11, i.e., 2-(4-(dimethylamino)phenyl)-5-(1-(p-tolyl)-1H-1,2,3-triazol-4-yl)-2H-imidazo[1,5-a]pyridin-4-ium chloride

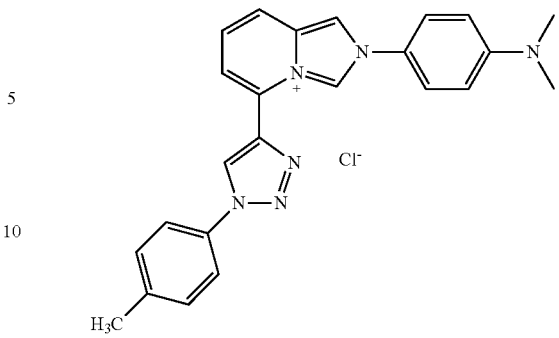

was prepared according to the General Procedure For Preparing Imidazo[1,5-a]pyridine Triazole Compounds: where the azide was 1-azido-4-methylbenzene, the amine was $N^1,N^1$-dimethylbenzene-1,4-diamine, and the copper source was copper (I) bromide dimethyl sulfide. The procedure was modified from the general procedure by using the bis-hydrochloric acid salt of the amine instead of 3 M hydrochloric acid in ethanol. The procedure was further modified by addition one equivalent of sodium hydroxide at the time of azide and copper addition.

Compound 12, i.e., 2-(4-(diethylamino)phenyl)-5-(1-(p-tolyl)-1H-1,2,3-triazol-4-yl)-2H-imidazo[1,5-a]pyridin-4-ium chloride,

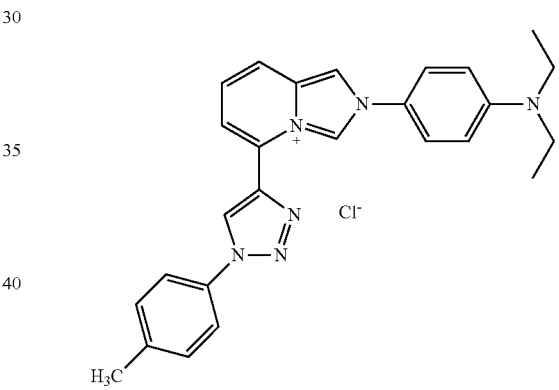

was prepared according to the General Procedure For Preparing Imidazo[1,5-a]pyridine Triazole Compounds: where the azide was 1-azido-4-methylbenzene, the amine was $N^1,N^1$-diethylbenzene-1,4-diamine, and the copper source was copper (I) bromide dimethyl sulfide. The procedure was modified from the general procedure by using the bis-hydrochloric acid salt of the amine instead of 3 M hydrochloric acid in ethanol. The procedure was further modified by addition one equivalent of sodium hydroxide at the time of azide and copper addition.

Figure 8A:
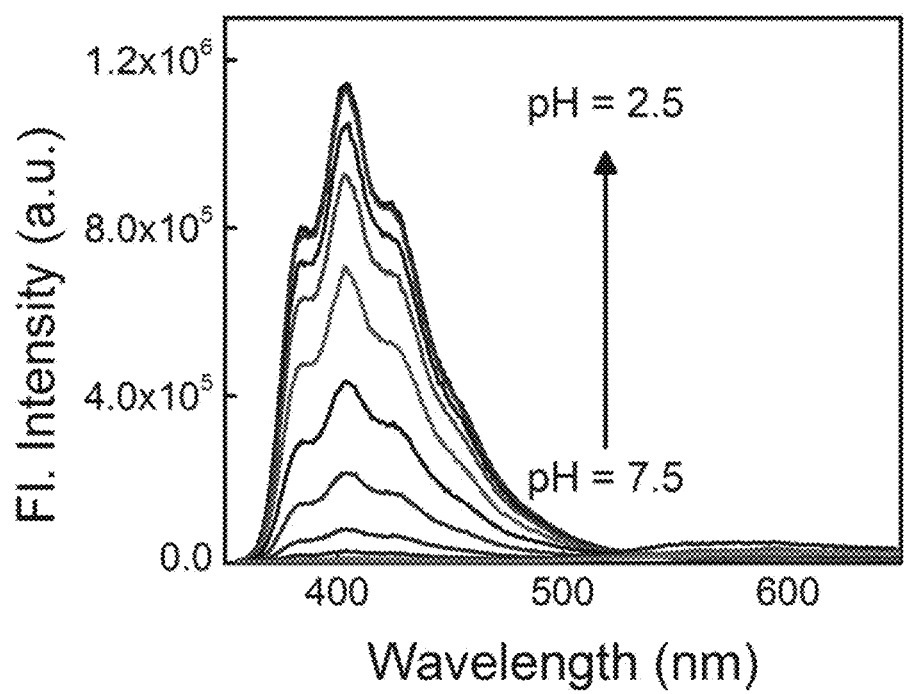
FIG. 8A is a plot of the fluorescence emission intensity versus wavelength of Compound 12 in buffered water solutions having a pH of from 2.5 to 7.5.

Compounds 10, 11, and 12 were each individually added, at a concentration of 30 μM, to water having a pH=7.5 and the emission spectra of each were obtained. At pH=7.5, the compounds exhibited essentially no fluorescence emission at 600 nm or at 400 nm. As the pH was decreased from 7.5 to 2.5 in 0.5 pH unit increments, fluorescence emission at 600 nm remained relatively nonexistent and the intensity of the fluorescence emission at 400 nm increased in correlation to the decrease in pH. FIG. 8A illustrates the emission properties of Compound 12. The emission properties illustrated in the plot of FIG. 8A are also representative of the emission properties exhibited by Compounds 10 and 11.

Figure 8B:
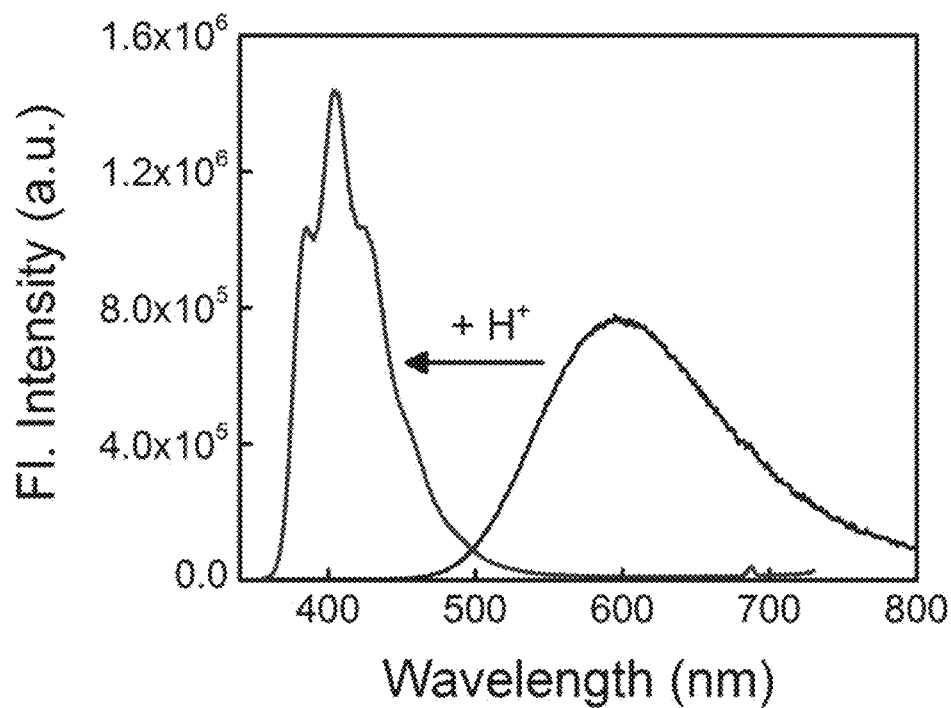
FIG. 8B is a plot of the fluorescence emission intensity versus wavelength of Compound 12 in acetonitrile with increasing acid concentration.

Compounds 10, 11, and 12 were then each individually added, at a concentration of 30 μM, to acetonitrile and the emission spectrum of each was monitored. The compounds emitted at 600 nm with an intensity of about 7.57×10⁵ arbitrary units (a.u.) in neat acetonitrile. When 50 μL trifluoroacetic acid was added to the acetonitrile, the compounds exhibited no emission at 600 nm but emitted at 400 nm with an intensity of 1.34×10⁶ a.u. FIG. 8B illustrates the emission properties of Compound 12. The emission properties illustrated in the plot of FIG. 8B are also representative of the emission properties exhibited by Compounds 10 and 11.

Example 18A

Figure 9A:
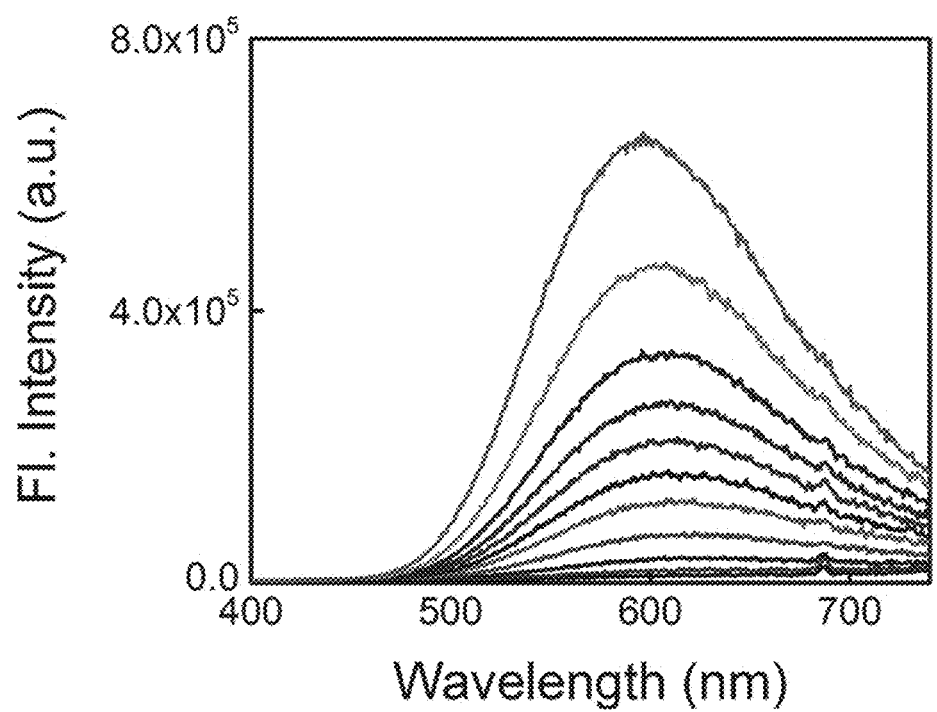
FIG. 9A is a plot of the fluorescence intensity versus wavelength of Compound 12 in water and with the addition of acetonitrile in amounts from 0 volume to volume (v/v) % to 100 v/v % in increments of 10 v/v %.
Figure 9B:
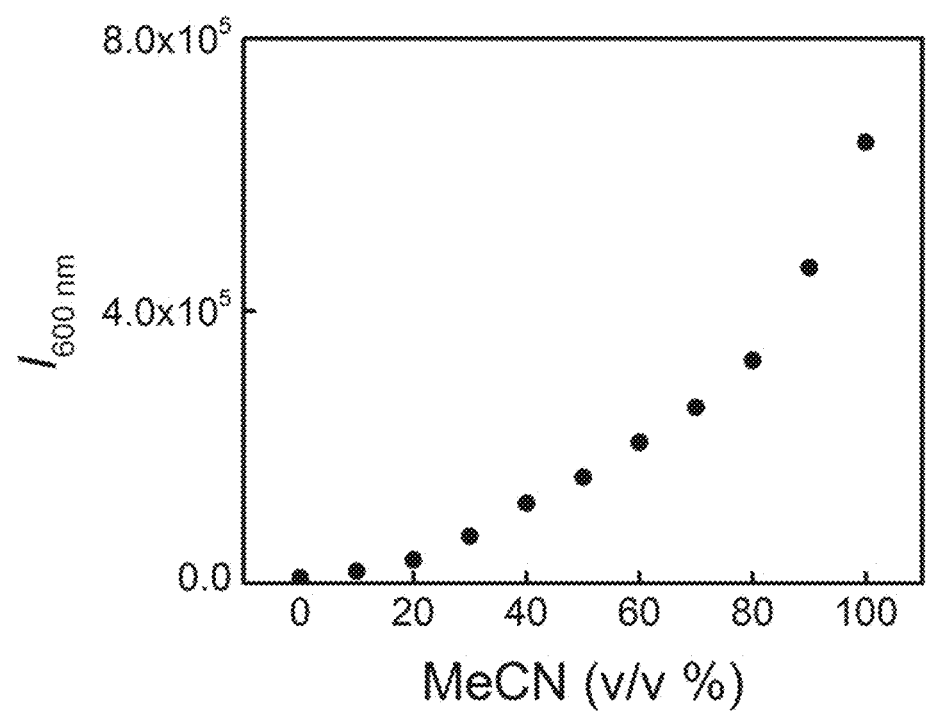
FIG. 9B is a plot of the fluorescence intensity of Compound 12 at 600 nm versus acetonitrile concentration in water as the concentration was increased in increments of 10 v/v %.

Compound 12 was placed in water and the intensity of its fluorescence emission at 600 nm was monitored as the concentration of acetonitrile was increased from 0 volume to volume (v/v) % to 100 v/v % in increments of 10 v/v %. As the acetonitrile concentration increased, a corresponding increase in fluorescence intensity occurred (from 7.81×10³ a.u. to 6.48×10⁵ a.u.), as illustrated in the plots of FIGS. 9A and 9B.

Example 18B

Compound 12 was added to an aqueous solution of sodium dodecylsulfate (SDS) and monitored for fluorescence emission at 600 nm. Compound 12 exhibited a similar increase in fluorescence emission intensity with increasing SDS concentration as seen in Example 14 with increasing acetonitrile concentration.

Example 19: Compound 13

Compound 13, i.e., 5-(1-(4-(dimethylamino)phenyl)-1H-1,2,3-triazol-4-yl)-2-(p-tolyl)-2H-imidazo[1,5-a]pyridin-4-ium chloride,

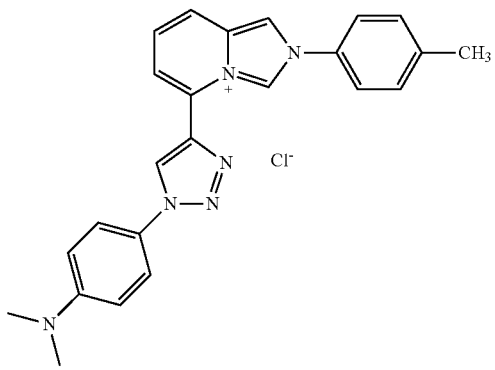

was prepared according to the General Procedure For Preparing Imidazo[1,5-a]pyridine Triazole Compounds: where the azide was 4-azido-N,N-dimethylaniline, the amine was p-toluidine, and the copper source was copper (I) bromide dimethyl sulfide.

Example 20: Compound 14

Compound 14, i.e., 5-(1-(4-(diethylamino)phenyl)-1H-1,2,3-triazol-4-yl)-2-(p-tolyl)-2H-imidazo[1,5-a]pyridin-4-ium chloride,

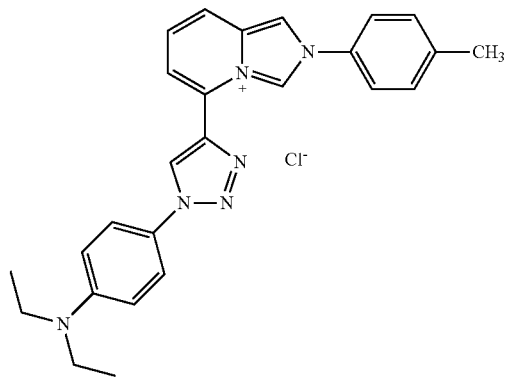

was prepared according to the General Procedure For Preparing Imidazo[1,5-a]pyridine Triazole Compounds: where the azide was 4-azido-N,N-diethylaniline, the amine was p-toluidine, and the copper source was copper (I) bromide dimethyl sulfide.

Example 21: Compound 15

Compound 15, i.e., 2-butyl-5-ethynyl-2H-imidazo[1,5-a]pyridin-4-ium chloride,

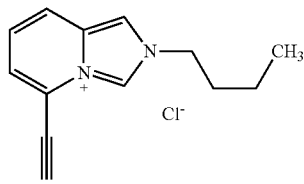

was prepared according to the General Procedure General Procedure (A) For Preparing Imidazo[1,5-a]pyridine Fluorophores: where the picolinaldehyde was 2-ethynyl picolinaldehyde, and the primary amine was n-butylamine. The procedure was modified from the general procedure by using the bis-hydrochloric acid salt of the amine instead of 3 M hydrochloric acid in ethanol.

Example 22: Compound 16

Compound 16, i.e., 2-(4-(dimethylamino)phenyl)-5-ethynyl-2H-imidazo[1,5-a]pyridin-4-ium chloride,

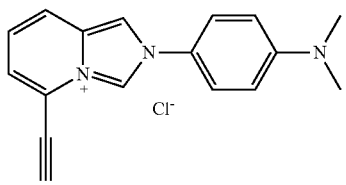

was prepared according to the General Procedure General Procedure (A) For Preparing Imidazo[1,5-a]pyridine Fluorophores: where the picolinaldehyde was 2-ethynyl picolinaldehyde, and the primary amine was $N^1,N^1$-dimethylbenzene-1,4-diamine. The procedure was modified from the general procedure by using the bis-hydrochloric acid salt of the amine instead of 3 M hydrochloric acid in ethanol. The workup was modified by dissolving crude material in an acetonitrile ethanol mixture (2:1) and stirring with an excess of solid sodium bicarbonate to remove excess acid. The bicarbonate was removed by filtration through a 0.2 μm nylon syringe tip filter.

Example 23: Compound 17

Compound 17, i.e., 5-(1-benzyl-1H-1,2,3-triazol-4-yl)-2-butyl-2H-imidazo[1,5-a]pyridin-4-ium tetraphenylborate,

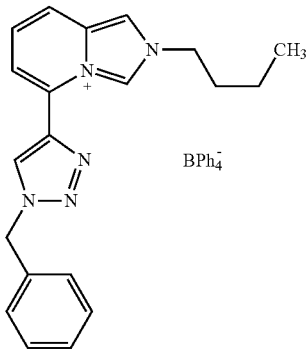

was prepared according to the General Procedure For Preparing Imidazo[1,5-a]pyridine Triazole Compounds: where the azide was benzylazide, the amine was n-butylamine, and the copper source was copper (I) bromide dimethyl sulfide.

Example 24: Compound 18

Compound 18, i.e., 2-butyl-5-(1-(4-(dimethylamino)phenyl)-1H-1,2,3-triazol-4-yl)-2H-imidazo[1,5-a]pyridin-4-ium tetraphenylborate,

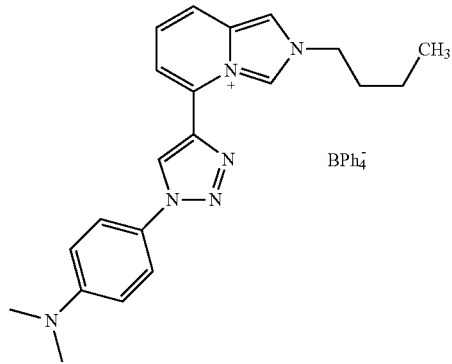

was prepared according to the General Procedure For Preparing Imidazo[1,5-a]pyridine Triazole Compounds: where the azide was 4-azido-N,N-dimethylaniline, the amine was n-butylamine, and the copper source was copper (I) bromide dimethyl sulfide.

Example 25: Compound 19

Compound 19, i.e., 2-(4-(dimethylamino)phenyl)-5-(1-(4-methoxyphenyl)-1H-1,2,3-triazol-4-yl)-2H-imidazo[1,5-a]pyridin-4-ium chloride,

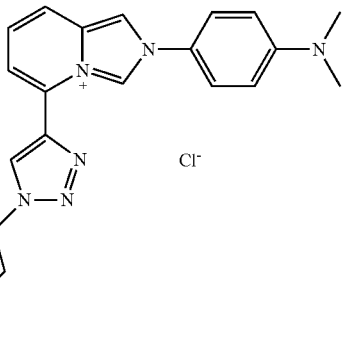

was prepared according to the General Procedure For Preparing Imidazo[1,5-a]pyridine Triazole Compounds: where the azide was 1-azido-4-methoxybenzene, the amine was $N^1,N^1$-dimethylbenzene-1,4-diamine, and the copper source was copper (I) bromide dimethyl sulfide. The procedure was modified from the general procedure by using the bis-hydrochloric acid salt of the amine instead of 3 M hydrochloric acid in ethanol. The procedure was further modified by addition one equivalent of sodium hydroxide at the time of azide and copper addition.

Example 26: Compound 20

Compound 20, i.e., 2-(4-(dimethylamino)phenyl)-5-(1-(4-(trifluoromethyl)phenyl)-1H-1,2,3-triazol-4-yl)-2H-imidazo[1,5-a]pyridin-4-ium chloride,

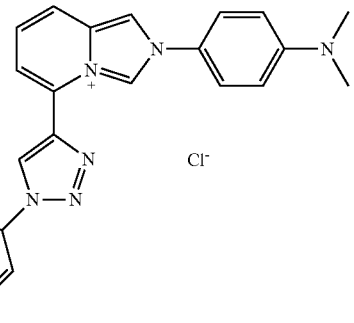

was prepared according to the General Procedure For Preparing Imidazo[1,5-a]pyridine Triazole Compounds: where the azide was 1-azido-4-(trifluoromethyl)benzene, the amine was $N^1,N^1$-dimethylbenzene-1,4-diamine, and the copper source was copper (I) bromide dimethyl sulfide. The procedure was modified from the general procedure by using the bis-hydrochloric acid salt of the amine instead of 3 M hydrochloric acid in ethanol. The procedure was further modified by addition one equivalent of sodium hydroxide at the time of azide and copper addition.

Example 27: Compound 21

Compound 21, i.e., 5-(4-(dimethylamino)phenyl)-2-(4-methoxyphenyl)-2H-imidazo[1,5-a]pyridin-4-ium tetraphenylborate,

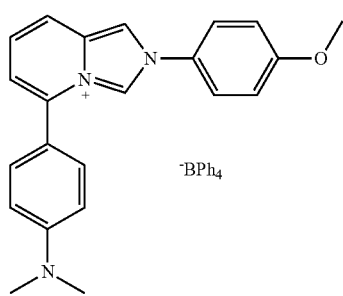

was prepared according to the General Procedure (A) For Preparing Imidazo[1,5-a]pyridine Fluorophores: where the picolinaldehyde was 6-(4-(dimethylamino)phenyl)picolinaldehyde, and the primary amine was 4-methoxyanaline. The procedure was modified from the general procedure by using two equivalents of 3 M hydrochloric acid in ethanol, as well as by running the reaction in an ethanol:chloroform mixture (1:1). The workup was modified by dissolving the crude material in an acetonitrile ethanol mixture (2:1) and stirring with an excess of solid sodium bicarbonate to remove excess acid. The bicarbonate was removed by filtration through a 0.2 μm nylon syringe tip filter. The tetraphenylborate salt was obtained by following through salt metathesis with sodium tetraphenylborate following the general procedure.

Compounds 6, 7, 9, 11-14 and 21 were analyzed according to: the Method for Obtaining Ultraviolet-Visible Light Spectrum to obtain the maximum absorbance wavelength ($\lambda_{abs,max}$), the Method for Obtaining Fluorescence Emission Spectrum to obtain the maximum emission wavelength ($\lambda_{em,max}$), and the Method for Determining Quantum Yield ($\Phi_F$) in the solvent and with the counter ion indicated in Table 3.

The compounds included hydrogen at each position that is not otherwise specified. Where the groups are specified, they are specified with reference to the following structure:

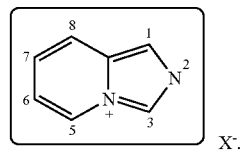

The compounds were present in the specified solvent at a concentration of 30 μM unless otherwise specified.

TABLE 3

| Compound | Solvent | Position of Group 1 | Group 1 | Position of Group 2 | Group 2 | Counter Ion | $\Phi_F$ % | $\lambda_{abs,max}$ Abs (nm) | $\lambda_{em,max}$ Em (nm) |
|---|---|---|---|---|---|---|---|---|---|
| 7 | MeCN | 1 | –C6H4–OCH3 | 2 | –C6H4–N(CH2CH3)2 | Cl− | 0 | 340 | NA |
| 7 | MeCN + 13.8 uL TFA | 1 | –C6H4–OCH3 | 2 | –C6H4–N(CH2CH3)2 | Cl− | 57 | 340 | 450 |
| 7 | H2O pH = 7.5 | 1 | –C6H4–OCH3 | 2 | –C6H4–N(CH2CH3)2 | Cl− | 0 | 340 | NA |
| 7 | H2O pH = 2.5 | 1 | –C6H4–OCH3 | 2 | –C6H4–N(CH2CH3)2 | Cl− | 42 | 340 | 450 |
| 6 | MeCN | 1 | –C6H4–N(CH2CH3)2 | 2 | –C6H4–OCH3 | Cl− | 59 | 350 | 565 |
| 6 | MeCN + 13.8 uL TFA | 1 | –C6H4–N(CH2CH3)2 | 2 | –C6H4–OCH3 | Cl− | 49 | 350 | 405 |
| 6 | H2O | 1 | –C6H4–N(CH2CH3)2 | 2 | –C6H4–OCH3 | Cl− | 16 | 350 | 580 |

TABLE 3-continued

| Compound | Solvent | Position of Group 1 | Group 1 | Position of Group 2 | Group 2 | Counter Ion | Φ_F % | λ_{abs,max} Abs (nm) | λ_{em,max} Em (nm) |
|---|---|---|---|---|---|---|---|---|---|
| 6 | H₂O pH = 2.5 | 1 | 4-(N(CH₂CH₃)₂)-phenyl | 2 | 4-OCH₃-phenyl | Cl⁻ | 31 | 350 | 400 |
| 9 | MeCN | 2 | —CH₂CH₂CH₂CH₃ | 5 | 4-N(CH₃)₂-phenyl | BPh₄⁻ | 75 | 350 | 490 |
| 21 | MeCN | 2 | 4-OCH₃-phenyl | 5 | 4-N(CH₃)₂-phenyl | BPh₄⁻ | 10 | 360 | 540 |
| 13 | MeCN | 2 | 4-CH₃-phenyl | 5 | 4-methyl-1-(4-(N(CH₃)₂)phenyl)-1H-1,2,3-triazol-4-yl | Cl⁻ | 0 | 340 | NA |
| 13 | MeCN + 50 μL TFA | 2 | 4-CH₃-phenyl | 5 | 4-methyl-1-(4-(N(CH₃)₂)phenyl)-1H-1,2,3-triazol-4-yl | Cl⁻ | 67 | 340 | 410 |
| 13 | H₂O pH = 7.5 | 2 | 4-CH₃-phenyl | 5 | 4-methyl-1-(4-(N(CH₃)₂)phenyl)-1H-1,2,3-triazol-4-yl | Cl⁻ | 0 | 340 | NA |
| 13 | H₂O pH = 2.5 | 2 | 4-CH₃-phenyl | 5 | 4-methyl-1-(4-(N(CH₃)₂)phenyl)-1H-1,2,3-triazol-4-yl | Cl⁻ | 59 | 340 | 405 |

TABLE 3-continued

| Compound | Solvent | Position of Group 1 | Group 1 | Position of Group 2 | Group 2 | Counter Ion | $\Phi_F$ % | $\lambda_{abs, max}$ Abs (nm) | $\lambda_{em, max}$ Em (nm) |
|---|---|---|---|---|---|---|---|---|---|
| 14 | MeCN | 2 | 4-methylphenyl | 5 | 4-methyl-1-(4-(diethylamino)phenyl)-1H-1,2,3-triazol-5-yl | Cl⁻ | 0 | 340 | NA |
| 14 | MeCN + excess TFA | 2 | 4-methylphenyl | 5 | 4-methyl-1-(4-(diethylamino)phenyl)-1H-1,2,3-triazol-5-yl | Cl⁻ | 64 | 340 | 410 |
| 14 | H₂O pH = 7.5 | 2 | 4-methylphenyl | 5 | 4-methyl-1-(4-(diethylamino)phenyl)-1H-1,2,3-triazol-5-yl | Cl⁻ | 0 | 340 | NA |
| 14 | H₂O pH = 2.2 | 2 | 4-methylphenyl | 5 | 4-methyl-1-(4-(diethylamino)phenyl)-1H-1,2,3-triazol-5-yl | Cl⁻ | 53 | 340 | 405 |
| 12 | MeCN | 2 | 4-(diethylamino)phenyl | 5 | 4-methyl-1-(4-methylphenyl)-1H-1,2,3-triazol-5-yl | Cl⁻ | 30 | 340 | 600 |

TABLE 3-continued

| Compound | Solvent | Position of Group 1 | Group 1 | Position of Group 2 | Group 2 | Counter Ion | $\Phi_F$ % | $\lambda_{abs, max}$ Abs (nm) | $\lambda_{em, max}$ Em (nm) |
|---|---|---|---|---|---|---|---|---|---|
| 12 | MeCN + 50 μL TFA | 2 | —C₆H₄—N(CH₂CH₃)₂ | 5 | 4-methyl-1-(4-methylphenyl)-1H-1,2,3-triazole | Cl⁻ | 57 | 340 | 400 |
| 12 | H₂O pH = 7.5 | 2 | —C₆H₄—N(CH₂CH₃)₂ | 5 | 4-methyl-1-(4-methylphenyl)-1H-1,2,3-triazole | Cl⁻ | 0 | 340 | NA |
| 12 | H₂O pH = 2.2 | 2 | —C₆H₄—N(CH₂CH₃)₂ | 5 | 4-methyl-1-(4-methylphenyl)-1H-1,2,3-triazole | Cl⁻ | 66 | 340 | 400 |
| 11 | MeCN | 2 | —C₆H₄—N(CH₃)₂ | 5 | 4-methyl-1-(4-methylphenyl)-1H-1,2,3-triazole | Cl⁻ | 35 | 400 | 605 |
| 11 | MeCN + 50 μL TFA | 2 | —C₆H₄—N(CH₃)₂ | 5 | 4-methyl-1-(4-methylphenyl)-1H-1,2,3-triazole | Cl⁻ | 55 | 340 | 405 |

TABLE 3-continued

| Compound | Solvent | Position of Group 1 | Group 1 | Position of Group 2 | Group 2 | Counter Ion | $\Phi_F$ % | $\lambda_{abs,max}$ Abs (nm) | $\lambda_{em,max}$ Em (nm) |
|---|---|---|---|---|---|---|---|---|---|
| 11 | H$_2$O pH = 7.5 | 2 | 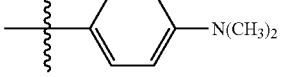 | 5 | 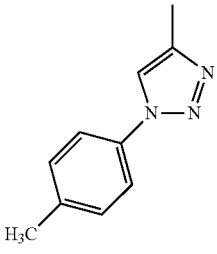 | Cl$^-$ | 0 | 340 | NA |
| 11 | H$_2$O pH = 2.5 | 2 |  | 5 | 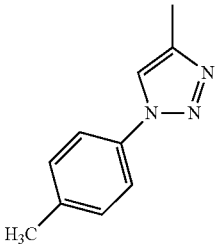 | Cl$^-$ | 29 | 340 | 400 |

MeCN = acetonitrile
H$_2$O = water
TFA = trifluoroacetic acid

All patents and other documents referred to herein are incorporated herein by reference.

Other embodiments are within the claims.

What is claimed is:

1. A fluorophore comprising:
a compound of the formula

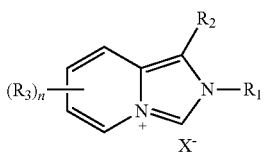

(I)

wherein

R$_1$ is alkyl, aryl, arylalkyl, glycoalkyl, haloalkyl, heteroaryl, heterocyclyl, or cycloalkyl, and when R$_1$ is aryl, heteroaryl, heterocyclyl, or cycloalkyl, R$_1$ optionally is substituted with at least one R$_4$, R$_2$ is H, alkyl, aryl, arylalkyl, carbonyl, cycloalkyl, cycloalkoxy, ether, thioether, halogen, haloalkyl, heteroaryl, or heterocyclyl, and when R$_2$ is aryl, heteroaryl, heterocyclyl or cycloalkyl, R$_2$ optionally is substituted with at least one R$_4$, R$_3$ is

[structure]

H, alkyl, alkoxy, alkenyl alkenoxy, alkynyl, alkynoxy, amide, amidino, amine, aryl, arylalkyl, azido, azo, carbamate, carbamide, carbonyl, carboxamido, carboxy, cycloalkyl, cycloalkoxy, ether, thioether, halogen, haloalkyl, heteroaryl, heterocyclyl, hydrazine, imino, nitro, phosphate, sulfate, sulfonamide, sulfonyl, sulfide, or thiocarbonyl, and when R$_3$ is alkenyl, alkenoxy, alkynyl, alkynoxy, aryl, heteroaryl, heterocyclyl or cycloalkyl, R$_3$ optionally is substituted with at least one R$_4$, each R$_4$ is independently H, alkyl, alkoxy, alkenyl, alkenoxy, alkynyl, alkynoxy, amide, amidino, amino, aryl, arylalkyl, azido, azo, carbamate, carbamide, carbonyl, carboxamido, carboxy, cycloalkyl, cycloalkoxy, cyano, ether, thioether, halogen, haloalkyl, heteroaryl, heterocyclyl, hydrazine, imino, nitro, phosphate, sulfate, sulfonamide, sulfonyl, sulfide, or thiocarbonyl, each R₅ is independently H, aryl, heteroaryl, ether, thioether, alkenyl, arylalkyl, cycloalkyl, haloalkyl, heteroaryl, or heterocyclyl, and when R₅ is alkenyl, aryl, heteroaryl, heterocyclyl or cycloalkyl, R₅ optionally is substituted with at least one R₄, X⁻ is a counter ion, and n is an integer from 1 to 4, the compound comprising at least one substituent comprising a heteroatom comprising at least one pair of electrons conjugated to the imidazo[1,5-a]pyridinium ion core, an aryl comprising a substituent comprising at least one pair of electrons conjugated to the aryl, an alkenyl, an alkynyl, or a combination thereof, and when $R_1$ comprises phenylalkoxy or phenylcyano, at least one of $R_2$ and $R_3$ is other than H.

2. The fluorophore of claim 1, wherein
   $R_1$ is $C_{1-4}$ alkyl, phenyl$C_{1-4}$ alkyl, phenyl$C_{1-4}$ alkoxy, or phenyl$C_{1-4}$ dialkylamine,
   $R_2$ is H, $C_{1-4}$ alkyl, phenyl$C_{1-4}$ alkyl, phenyl$C_{1-4}$ alkoxy, or phenyl$C_{1-4}$ dialkylamine, and
   $R_3$ is H, $C_{1-4}$ alkyl, phenyl$C_{1-4}$ alkyl, phenyl$C_{1-4}$ alkoxy, or phenyl$C_{1-4}$ dialkylamine.

3. The fluorophore of claim 1, wherein $R_5$ is each Z is independently CH or N, and each $R_6$ is independently alkyl, alkoxy, amine, aryl, heteroaryl, halo, haloalkyl, hydrogen, nitro, carboxy, ester, ether, thioether, phosphate, sulfate, sulfonamide, sulfonyl, sulfide, or thiocarbonyl, optionally substituted with at least one $R_4$.

4. The fluorophore of claim 1, wherein at least one of $R_1$, $R_2$ and $R_3$ is phenyl(diacetic acid)amine, phenyl(dimethylpyridyl)amine, phenyl(methylpyridyl)(methylthiophene)amine, a phenyl substituted with a crown ether or a phenyl substituted with an aza-crown ether.

5. The fluorophore of claim 1, wherein the compound exhibits a change in the intensity of the fluorescence emitted, a change in the wavelength of fluorescence emitted or a combination thereof in response to the presence of a cation.

6. The fluorophore of claim 1, wherein the compound binds at least two different cations.

7. The fluorophore of claim 1, wherein the compound has the formula (I)

8. The fluorophore of claim 7, wherein
   $R_1$ is $C_{1-4}$ alkyl, phenyl$C_{1-4}$ alkyl, phenyl$C_{1-4}$ alkoxy, or phenyl$C_{1-4}$ dialkylamine,
   $R_2$ is H, $C_{1-4}$ alkyl, phenyl$C_{1-4}$ alkyl, phenyl$C_{1-4}$ alkoxy, or phenyl$C_{1-4}$ dialkylamine, and
   $R_3$ is H, $C_{1-4}$ alkyl, phenyl$C_{1-4}$ alkyl, phenyl$C_{1-4}$ alkoxy, or phenyl$C_{1-4}$ dialkylamine.

9. The fluorophore of claim 1, wherein the compound is selected from the group consisting of 2-(4-(diethylamino)phenyl)-2H-imidazo[1,5-a]pyridin-4-ium hexafluorophosphate, 2-butyl-1-(4-methoxyphenyl)-2H-imidazo[1,5-a]pyridin-4-ium chloride, 2-butyl-1-(4-(diethylamino)phenyl)-2H-imidazo[1,5-a]pyridin-4-ium tetraphenylborate, 1-(4-(diethylamino)phenyl)-2-(4-methoxyphenyl)-2H-imidazo[1,5-a]pyridin-4-ium chloride, 2-(4-(diethylamino)phenyl)-1-(4-methoxyphenyl)-2H-imidazo[1,5-a]pyridin-4-ium chloride, 2-(4-(dimethylamino)-2,6-diisopropylphenyl)-2H-imidazo[1,5-a]pyridin-4-ium tetraphenylborate, 5-(1-benzyl-1H-1,2,3-triazol-4-yl)-2-butyl-2H-imidazo[1,5-a]pyridin-4-ium tetraphenylborate, 2-butyl-5-(1-(4-(dimethylamino)phenyl)-1H-1,2,3-triazol-4-yl)-2H-imidazo[1,5-a]pyridin-4-ium tetraphenylborate, 5-(1-(4-(dimethylamino)phenyl)-1H-1,2,3-triazol-4-yl)-2-(p-tolyl)-2H-imidazo[1,5-a]pyridin-4-ium chloride, 5-(1-(4-(diethylamino)phenyl)-1H-1,2,3-triazol-4-yl)-2-(p-tolyl)-2H-imidazo[1,5-a]pyridin-4-ium chloride, 5-(1-(4-(diethylamino)phenyl)-1H-1,2,3-triazol-4-yl)-2-(4-(dimethylamino)phenyl)-2H-imidazo[1,5-a]pyridin-4-ium chloride, 5-(1-(4-((diethylamino)methyl)phenyl)-1H-1,2,3-triazol-4-yl)-2-(4-(dimethylamino)phenyl)-2H-imidazo[1,5-c]pyridin-4-ium chloride, 2-(4-(dimethylamino)phenyl)-5-(1-(4-(trifluoromethyl)phenyl)-1H-1,2,3-triazol-4-yl)-2H-imidazo[1,5-a]pyridin-4-ium chloride, 2-(4-(dimethylamino)phenyl)-5-(1-(4-methoxyphenyl)-1H-1,2,3-triazol-4-yl)-2H-imidazo[1,5-a]pyridin-4-ium chloride, 2-(4-(diethylamino)phenyl)-5-ethynyl-2H-imidazo[1,5-a]pyridin-4-ium chloride, 2-butyl-5-ethynyl-2H-imidazo[1,5-a]pyridin-4-ium chloride, 2-(4-(dimethylamino)phenyl)-5-ethynyl-2H-imidazo[1,5-a]pyridin-4-ium chloride, 5-(4-(dimethylamino)phenyl)-2-(4-methoxyphenyl)-2H-imidazo[1,5-a]pyridin-4-ium tetraphenylborate, 2-butyl-5-(4-(dimethylamino)phenyl)-2H-imidazo[1,5-a]pyridin-4-ium tetraphenylborate, (diethylamino)phenyl)-3-(pyridin-2-yl)-2H-imidazo[1,5-a]pyridin-4-ium hydrogensulfate, 2-(4-(diethylamino)phenyl)-2H-imidazo[1,5-a]pyridin-4-ium hydrogensulfate, 2-(4-(diethylamino)phenyl)-5-(1-(p-tolyl)-

1H-1,2,3-triazol-4-yl)-2H-imidazo[1,5-a]pyridin-4-ium chloride, 2-(4-(dimethylamino)phenyl)-5-(1-(p-tolyl)-1H-1,2,3-triazol-4-yl)-2H-imidazo[1,5-a]pyridin-4-ium chloride, 2-butyl-5-(4-(dimethylamino)phenyl)-2H-imidazo[1,5-a]pyridin-4-ium tetraphenylborate, and 5-(4-(dimethylamino)phenyl)-2-(4-methoxyphenyl)-2H-imidazo[1,5-a]pyridin-4-ium tetraphenylborate.

10. A cation sensor comprising the fluorophore of claim 1.

11. A cation sensor comprising the fluorophore of claim 1, wherein the compound comprises a first substituent comprising at least one of
- a heteroatom comprising at least one pair of electrons conjugated to the imidazo[1,5-a]pyridinium ion core, and
- an aryl comprising a second substituent comprising a heteroatom comprising at least one pair of electrons conjugated to the aryl.

12. A compound of the formula

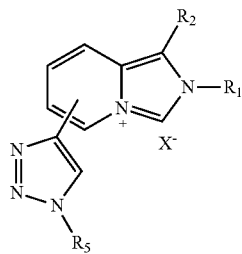

wherein
- $R_1$ is alkyl, aryl, arylalkyl, glycoalkyl, haloalkyl, heteroaryl, heterocyclyl, or cycloalkyl, and when $R_1$ is aryl, heteroaryl, heterocyclyl, or cycloalkyl, $R_1$ optionally is substituted with at least one $R_4$,
- $R_2$ is H, alkyl, aryl, arylalkyl, carbonyl, cycloalkyl, ether, thioether, halogen, haloalkyl, heteroaryl, or heterocyclyl, and when $R_2$ is alkenyl, aryl, heteroaryl, heterocyclyl or cycloalkyl, $R_2$ optionally is substituted with $R_4$,
- each $R_5$ is independently H, aryl, heteroaryl, ether, thioether, alkyl, alkenyl, arylalkyl, cycloalkyl, haloalkyl, heteroaryl, or heterocyclyl, and when $R_5$ is alkenyl, aryl, heteroaryl, heterocyclyl or cycloalkyl, $R_5$ optionally is substituted with at least one $R_4$,
- each $R_4$ is independently alkyl, alkoxy, or amine, and at least one $R_4$ is amine, and at least one of $R_1$, $R_2$ and $R_5$ comprises

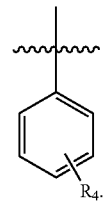

13. The compound of claim 12, wherein $R_1$ is aryl.

14. The compound of claim 12, wherein $R_5$ and $R_1$ are aryl and at least one of $R_1$ and $R_5$ is arylamine.

15. The compound of claim 12, wherein $R_5$ is arylamine and $R_1$ is arylamine.

16. The compound of claim 12, wherein the compound has the formula

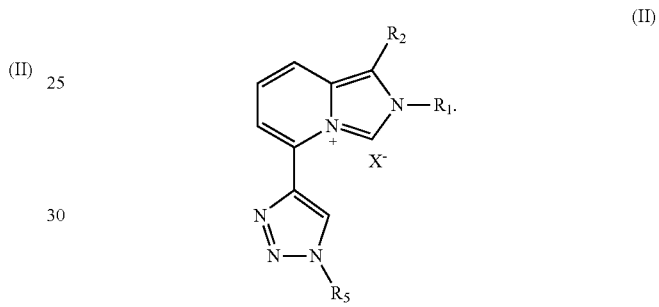

17. The compound of claim 16, wherein $R_1$ is aryl.

18. The compound of claim 16, wherein $R_5$ and $R_1$ are aryl and at least one of $R_1$ and $R_5$ is arylamine.

19. The compound of claim 16, wherein $R_1$ is arylamine.

20. The compound of claim 16, wherein $R_5$ and $R_1$ are arylamine.

21. A method of staining tissue, the method comprising:
contacting a tissue with a compound of claim 1;
exciting the compound with radiation; and
detecting fluorescence emitted by the tissue.

22. A method of staining tissue, the method comprising:
contacting a tissue with a compound of claim 12;
exciting the compound with radiation; and
detecting fluorescence emitted by the tissue.

23. A method of staining tissue, the method comprising:
contacting a tissue with a compound of claim 16;
exciting the compound with radiation; and
detecting fluorescence emitted by the tissue.

* * * * *